(12) United States Patent
Wensrich et al.

(10) Patent No.: US 11,413,137 B2
(45) Date of Patent: Aug. 16, 2022

(54) IOL INJECTOR HAVING A COLLAPSIBLE MECHANISM AND/OR A LEVER-DRIVEN RACK AND PINION

(71) Applicant: Alcon Inc., Fribourg (CH)

(72) Inventors: Douglas Brent Wensrich, Bedford, TX (US); Len Takudzwa Magara, Ithica, NY (US); Jian Liu, Keller, TX (US); Anubhav Chauhan, Benbrook, TX (US)

(73) Assignee: Alcon Inc., Fribourg (CH)

( * ) Notice: Subject to any disclaimer, the term of this patent is extended or adjusted under 35 U.S.C. 154(b) by 432 days.

(21) Appl. No.: 16/712,044

(22) Filed: Dec. 12, 2019

(65) Prior Publication Data

US 2020/0197167 A1    Jun. 25, 2020

Related U.S. Application Data

(60) Provisional application No. 62/782,613, filed on Dec. 20, 2018.

(51) Int. Cl.
*A61F 2/16* (2006.01)
(52) U.S. Cl.
CPC ............ *A61F 2/1672* (2013.01); *A61F 2/167* (2013.01); *A61F 2/1691* (2013.01)

(58) Field of Classification Search
CPC ...... A61F 2/167; A61F 2/1672; A61F 2/1662; A61F 2/1667; A61F 2/1681; A61F 2/16; A61F 2250/0007; A61F 2002/1681; A61F 2002/1683; A61F 2/1691
USPC .......................................................... 606/107
See application file for complete search history.

(56) References Cited

U.S. PATENT DOCUMENTS

| 4,411,656 | A | 10/1983 | Cornett, III |
| 7,156,854 | B2 | 1/2007 | Brown et al. |
| 9,700,407 | B2 | 7/2017 | Safabash |
| 2007/0050023 | A1 | 3/2007 | Bessiere et al. |
| 2010/0106160 | A1* | 4/2010 | Tsai ................. A61F 2/167 606/107 |
| 2016/0256316 | A1 | 9/2016 | Van Noy et al. |
| 2017/0245984 | A1* | 8/2017 | Germann .......... A61M 5/31581 |

FOREIGN PATENT DOCUMENTS

WO    2009002789 A1    12/2008

\* cited by examiner

*Primary Examiner* — Tan-Uyen T Ho
*Assistant Examiner* — Bridget E. Rabaglia

(57) ABSTRACT

An IOL injector having a collapsible mechanism and/or a lever-driven rack and pinion is described.

20 Claims, 14 Drawing Sheets

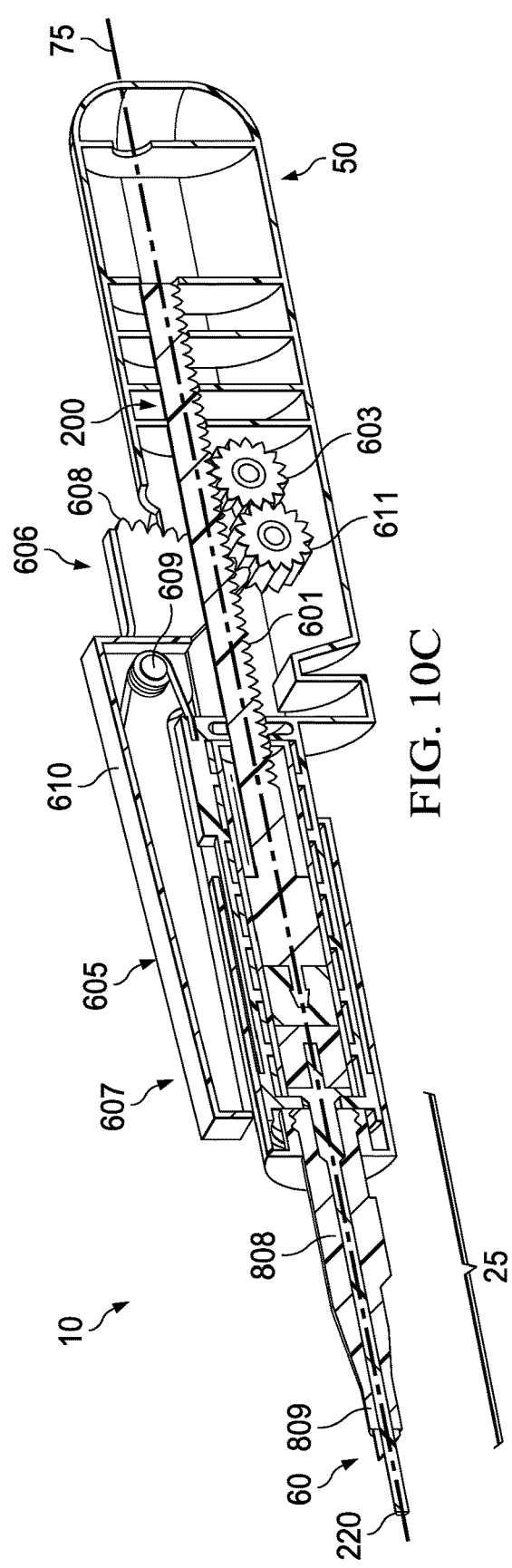
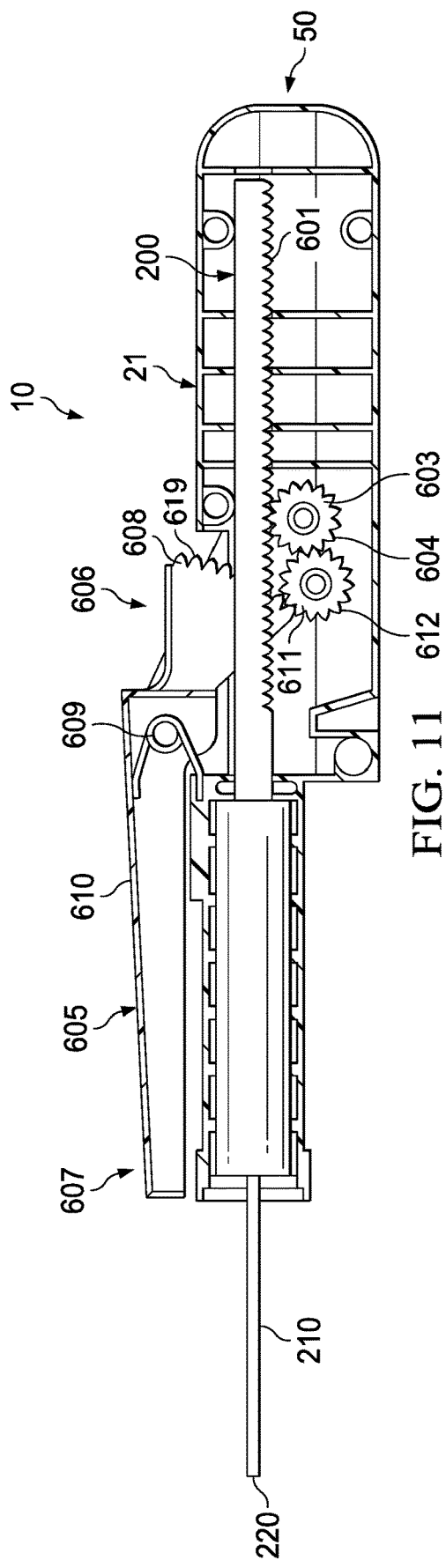
FIG. 10C
FIG. 11

IOL INJECTOR HAVING A COLLAPSIBLE MECHANISM AND/OR A LEVER-DRIVEN RACK AND PINION

TECHNICAL FIELD

The present disclosure relates to systems, apparatuses, and methods for intraocular lens (IOL) injectors.

BACKGROUND

The human eye in its simplest terms functions to provide vision by transmitting and refracting light through a clear outer portion called the cornea, and further focusing the image by way of the lens onto the retina at the back of the eye. The quality of the focused image depends on many factors including the size, shape, and length of the eye, and the shape and transparency of the cornea and lens. When trauma, age, or disease cause the lens to become less transparent, vision deteriorates because of the diminished light which can be transmitted to the retina. This deficiency in the lens of the eye is medically known as a cataract. The treatment for this condition is surgical removal of the lens and implantation of an artificial lens (the IOL).

Many cataractous lenses are removed by a surgical technique called phacoemulsification. During this procedure, an opening is made in the anterior capsule of an eye and a phacoemulsification cutting tip is inserted into the diseased lens and vibrated ultrasonically. The vibrating cutting tip liquifies or emulsifies the lens so that the lens may be aspirated out of the eye. The diseased lens, once removed, is replaced with an IOL.

The IOL may be injected into the eye through a small incision, sometimes the same incision used to remove the diseased lens. An IOL injector may be used to deliver an IOL into the eye.

SUMMARY

According to a first aspect, the present disclosure relates to an IOL injector which may include a main body having a proximal end, a distal end, and a distal portion including the distal end. The IOL injector may also include a collapsible portion forming a telescoping cylinder and including at least a first sleeve including a proximal end and a distal end and a second sleeve slideably coupled with the first sleeve and formed from the distal portion of the main body and having a proximal end and a distal end. In an uncollapsed configuration, the distal end of the second sleeve may be adjacent to the proximal end of the first sleeve, and, in a collapsed configuration, the distal end of the second sleeve may be adjacent to the distal end of the first sleeve. The IOL injector may further include a nozzle having a proximal end and a distal end, the proximal end coupled to the distal end of the first sleeve of the collapsible portion, the nozzle further including an IOL storage location and an IOL dwell position distal to the IOL storage location, a bore including a longitudinal axis extending from the proximal end of the main body to the distal end of the nozzle, and a plunger movably coupled concentrically within the injector body and aligned within the bore, the plunger including a plunger tip adapted to contact an IOL. In the uncollapsed configuration, the plunger tip may be in a first position proximally adjacent to the IOL storage location, and, in the collapsed configuration, the plunger tip may be in a second position proximally adjacent to the IOL dwell position. The IOL injector may have a length which, in the collapsed configuration, may be 10 to 20% shorter than in the uncollapsed configuration. The second sleeve may be slideably coupled concentrically within the first sleeve. The first sleeve may be slideably coupled concentrically within the second sleeve.

According to a second aspect, the present disclosure relates to an IOL injector which may include a lever-driven rack and pinion system. The IOL injector may include an injector body including a main body including a proximal end and a distal end, a nozzle including a proximal end and a distal end, the proximal end of the nozzle coupled to the distal end of the main body, and a bore including a longitudinal axis extending from the proximal end of the main body to the distal end of the nozzle. The IOL injector may also include at least one pinion including a plurality of teeth. The IOL injector may further include a lever having a distal end, a pivot point located between the proximal end of the lever and the distal end and rotatably coupled to the injector body to allow a rotational movement of the lever about the pivot point, a depressible surface accessible to a user and located between the pivot point and the distal end of the lever, and a proximal end including an arcuate rack including a plurality of teeth adapted to interface with a plurality of teeth of one pinion and rotationally move the pinion in response to movement of the arcuate rack. The IOL injector may further include a plunger movably coupled concentrically within the injector body and aligned within the bore, the plunger including a plunger body including a proximal end and a distal end and further including a plunger rack including a plurality of teeth adapted to interface with a plurality of teeth of one pinion and the plunger rack further adapted to be linearly moveable towards the distal end of the nozzle in response to rotational movement of one pinion, a plunger rod including a proximal end and a distal end, the proximal end of the plunger rod coupled to the distal end of the plunger body, and a plunger tip formed at the distal end of the plunger rod and adapted to contact an IOL and move the IOL from a dwell position in response to a depression of the surface of the lever. The IOL injector may include one pinion and the plurality of teeth of the arcuate rack may be adapted to interface with the plurality of teeth of the pinion, the plurality of teeth of the plunger rack may be adapted to interface with the plurality of teeth of the pinion, in response to the depression of the depressible surface of the lever, the lever may be adapted to rotate about the pivot point in a first rotational direction and move the plurality of teeth of the arcuate rack in the first rotational direction, and the pinion may be adapted to rotate in a second rotational direction, and the plunger rack may be adapted to be linearly moveable towards the distal end of the nozzle in response to the rotational movement of the pinion in the second rotational direction. The IOL injector may include two pinions and the plurality of teeth of the arcuate rack may be adapted to interface with a plurality of teeth of a first pinion, the plurality of teeth of the first pinion may be adapted to interface with a plurality of teeth of a second pinion, the plurality of teeth of the plunger rack may be adapted to interface with the plurality of teeth of the second pinion, in response to the depression of the depressible surface of the lever, the lever may be adapted to rotate about the pivot point in a first rotational direction and move the plurality of teeth of the arcuate rack in the first rotational direction, the first pinion may be adapted to rotate in a second rotational direction, and the second pinion may be adapted to rotate in the first rotational direction, and the plunger rack may be adapted to be linearly movable towards the distal end of the nozzle in response to the rotational movement of the second pinion in the first rotational direction. The first pinion may further include a pawl, the second pinion may further include a ratchet, and the pawl may be adapted to interface with the ratchet to prevent movement of the plunger rack toward the proximal end of the nozzle. The first pinion may have a circumference R1, the second pinion may have a circumference R2, and the ratio of the value of R2 to R1 may be from 1:1 to 1:5. The IOL injector may further include a reset spring having a first end coupled to the lever and a second end coupled to the injector body, the lever may be adapted to rotate in a first rotational direction in response to a depression of the depressible surface of the lever, and the reset spring may be adapted to rotate the lever in a second rotational direction opposite the first rotational direction. The nozzle may have an IOL storage location and an IOL dwell position, the IOL dwell position distal to the IOL storage location, a distance between the IOL dwell position and the distal end of the nozzle may have a length r, and the plunger rack may be adapted to move a distance of length r in response to 1 to 10 depressions of the lever. The injector body may be collapsible and the IOL injector may further include a main body having a proximal end, a distal end, and a distal portion including the distal end and a collapsible portion forming a telescoping cylinder and having at least a first sleeve having a proximal end and a distal end and a second sleeve slideably coupled with the first sleeve and formed from the distal portion of the main body and having a proximal end and a distal end and, in an uncollapsed configuration, the distal end of the second sleeve may be adjacent to the proximal end of the first sleeve, and, in a collapsed configuration, the distal end of the second sleeve may be adjacent to the distal end of the first sleeve. The plurality of teeth of the plunger rack may interface with the plurality of teeth of the pinion when the IOL injector is in the collapsed configuration, but not when the IOL injector is in the uncollapsed configuration. The plunger body may further include a flange adapted to contact the proximal end of the plunger body, the plunger body may be adapted to move axially in response to an axial force applied to the flange, and the plunger tip may be adapted to move the IOL from a storage location to the dwell position in response to the axial force applied to the flange. The IOL injector may further include a ribbed damping mechanism including at least one rib on the plunger body and at least one rib on an interior wall of the bore and the at least one rib on the plunger may be adapted to contact the at least one rib on the interior wall and to provide a frictional resistance to axial movement of the plunger. One or more of the ribs on the plunger body may form a ridge and one or more ribs on the interior wall may form a ridge-engaging tooth and the ridge and the ridge-engaging tooth may be adapted to prevent movement of the plunger toward the proximal end of the main body of the IOL injector. One or more of the ribs on the interior wall may form a ridge and one or more ribs on the plunger may form a ridge-engaging tooth and the ridge and the ridge-engaging tooth may be adapted to prevent movement of the plunger toward the proximal end of the main body of the IOL injector. The IOL injector may be adapted to separately inject an IOL base, an IOL optic, or both. The IOL injector may be adapted to concurrently inject an IOL base and an IOL optic.

BRIEF DESCRIPTION OF THE DRAWINGS

For a more complete understanding of the present disclosure, reference is now made to the following description, taken in conjunction with the accompanying drawings, which are not to scale, and in which:

FIG. 10C is yet another cross-sectional view of an example IOL injector having a collapsible portion of an injector body and a lever-driven rack and pinion system of FIG. 10A, in which the collapsible portion of the injector body has been collapsed and the plunger has been advanced to the distal end of the IOL injector by the lever-driven rack and pinion system;

FIG. 11 is a cross-sectional view of an example IOL injector having a lever-driven rack and pinion system, but not a collapsible portion;

DETAILED DESCRIPTION

Figure 1:
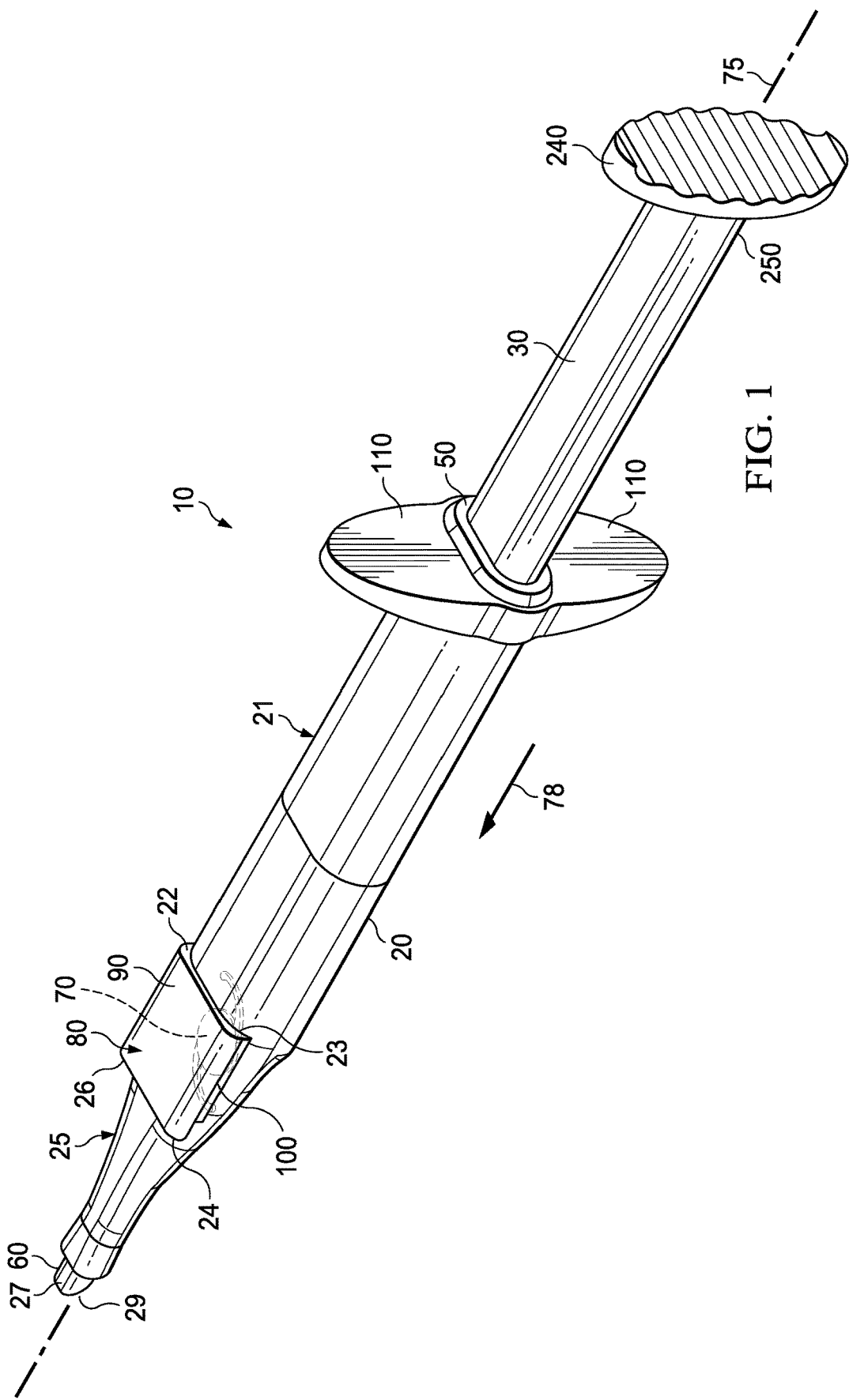
FIG. 1 is a perspective view of an example IOL injector.

For the purposes of promoting an understanding of the principles of the present disclosure, reference will now be made to the implementations illustrated in the drawings, and specific language will be used to describe the same. It will nevertheless be understood that no limitation of the scope of the disclosure is intended. Any alterations and further modifications to the described devices, instruments, methods, and any further application of the principles of the present disclosure are fully contemplated as would normally occur to one skilled in the art to which the disclosure relates. In particular, it is fully contemplated that the features, components, and/or steps described with respect to one implementation may be combined with the features, components, and/or steps described with respect to other implementations of the present disclosure.

Figure 2:
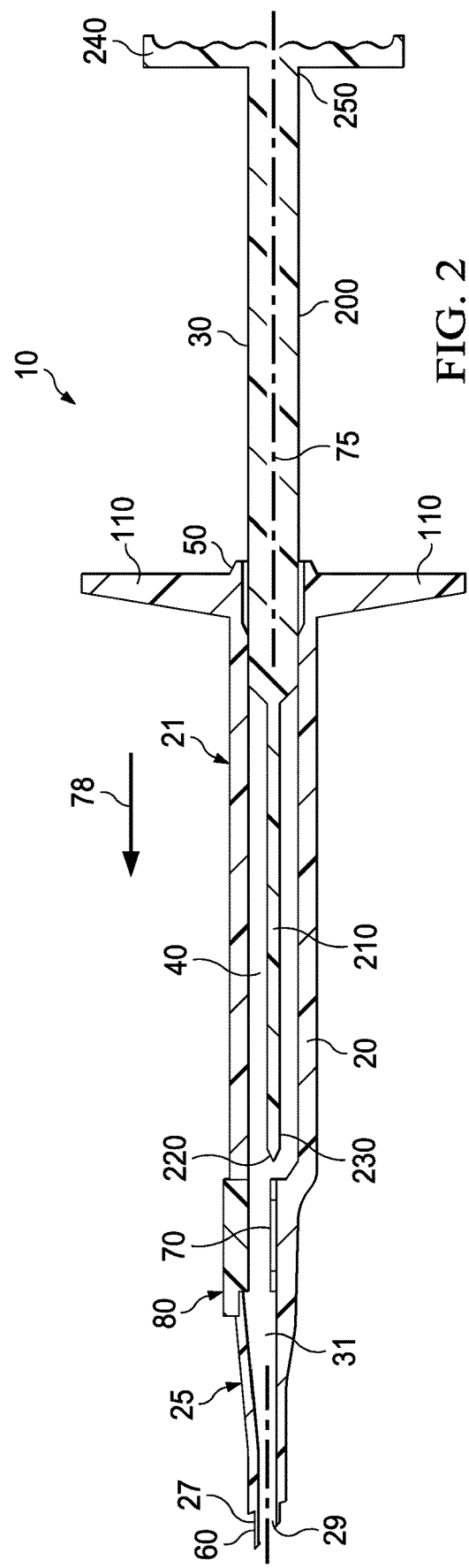
FIG. 2 is a longitudinal cross-sectional view of the IOL injector of FIG. 1.

FIGS. 1 and 2 are exemplary schematics of an example IOL injector 10 that is actuated by manual user application of force. The IOL injector 10 includes an injector body 20, a plunger 30 adapted to reciprocate through a bore 40 formed in the injector body 20, a folding device 80, and a nozzle 25 disposed at a distal end 60 of the injector body 20.

The IOL injector 10 also includes a longitudinal axis 75. The longitudinal axis 75 may extend along the plunger 30 and define a longitudinal axis of the plunger 30.

The IOL injector 10 includes a main body 21, having a proximal end 50 and a distal end 22. The distal end 22 of the main body 21 is coupled to a proximal end 23 of the folding device 80. The distal end 24 of the folding device 80 is coupled to the proximal end 26 of the nozzle 25. The nozzle 25 defines a passage 31 through which a folded IOL may be advanced and delivered into an eye via an opening 29 in distal tip 27 at distal end 60. A delivery channel of the folding device 80 may be aligned with the bore 40 in order to advance an IOL, such as IOL 70, within the delivery channel of the folding device 80 and the passage 31 of the nozzle 25 to allow delivery through tip 27 into the eye.

The folding device 80 may include a door 90 to provide access to the interior of the folding device 100. The door 90 may include a hinge 100 such that the door 90 may be pivoted about the hinge 100 to open the folding device 80 and, for example, allow the installation of the IOL 70. In other implementations, the folding device 80 may exclude a door for installing the IOL 70. In such instances, the IOL 70 may be incorporated into the folding device 80 at the time of assembly of the folding device 80. Thus, in such instances, the IOL injector 10 would be a preloaded IOL injector.

The injector body 20 may also include tabs 110 formed at the proximal end 50 of the injector body 20. The tabs 110 may be manipulated by fingers of a user, such as an ophthalmologist, an ophthalmic surgical assistant or nurse, or other medical professional, to advance the plunger 30 through the bore 40. The plunger 30 may include a body portion 200, a plunger rod 210 extending distally from the body portion 200, and a plunger tip 220 formed at the distal end 230 of the plunger rod 210 and adapted to contact the folded IOL disposed, for example, with the folding device 80 of the IOL injector 10. As the plunger 30 is displaced distally within the bore 40 in the direction of the arrow 78, the plunger tip 220 of the plunger 30 engages and advances the folded IOL, such as IOL 70, contained in the folding device 80. The plunger 30 may also include flanges 240 formed at proximal end 250, which may be manipulated by the finger or hand of the user to advance the plunger 30 through the bore 40 by displacing the plunger 30 through the bore 40 distally in the direction of the arrow 78.

In some implementations described herein, various parts of the plunger 30 may be physically separated or decoupled from each other within the injector body 20 of the IOL injector 10. For example, in some implementations, the plunger body 200 may be physically separated or decoupled from the plunger rod 210. In various implementations, where various parts of the plunger 30 are physically separated or decoupled from each other, additional components of the IOL injector 10 may actuate movement of one part of the plunger 30 in response to movement of another part of the plunger 30, as will be apparent to persons of ordinary skill in the art upon reading of the present disclosure.

Figure 3:
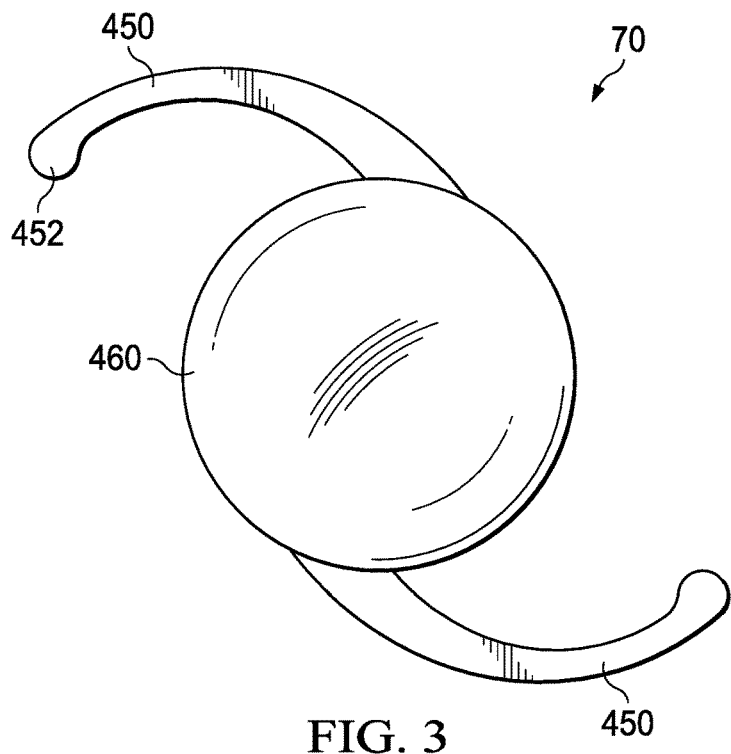
FIG. 3 shows an example one-piece IOL.

In some implementations, the IOL 70 may be a one-piece IOL. That is, in some implementations, the IOL 70 may include an optic 460 and haptics 450, as shown in FIG. 3. Each of the haptics 450 include a tip 452. In some implementations, the optic 460 and the haptics 450 may be integrally formed out of a single piece of material. In other implementations, the optic 460 may be formed out of one piece of material; the haptics 450 may be formed out of another piece of material, and the optic 460; and the haptics 450 may be coupled together prior to delivery into an eye. In some instances, the optic 460 and haptics 450 may be fixedly secured to each other prior to insertion into an IOL injector and delivered into an eye.

Figure 4:
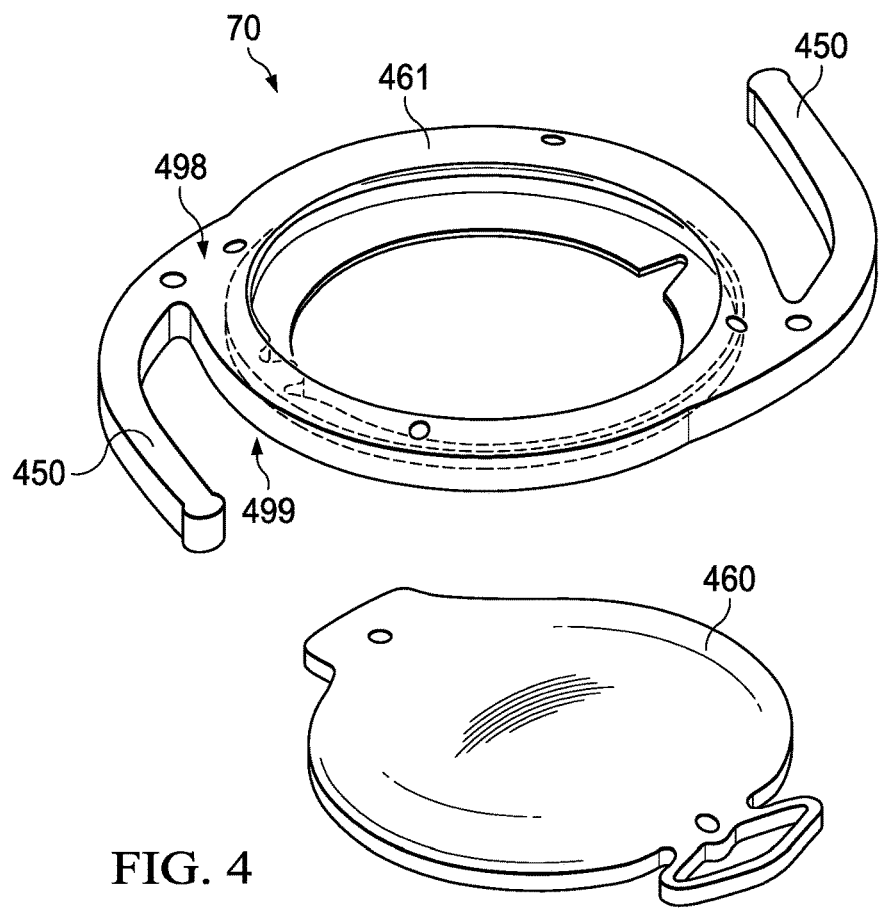
FIG. 4 shows an example two-piece IOL including a base and an optic.
Figure 5:
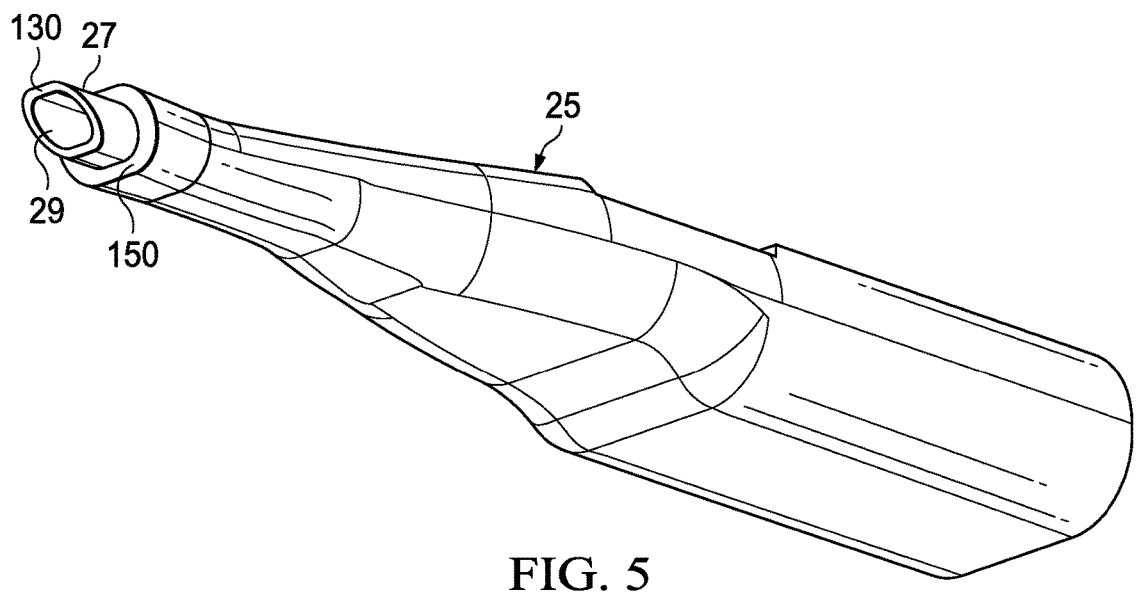
FIG. 5 is a perspective view of an example nozzle of an IOL injector.
Figure 6:
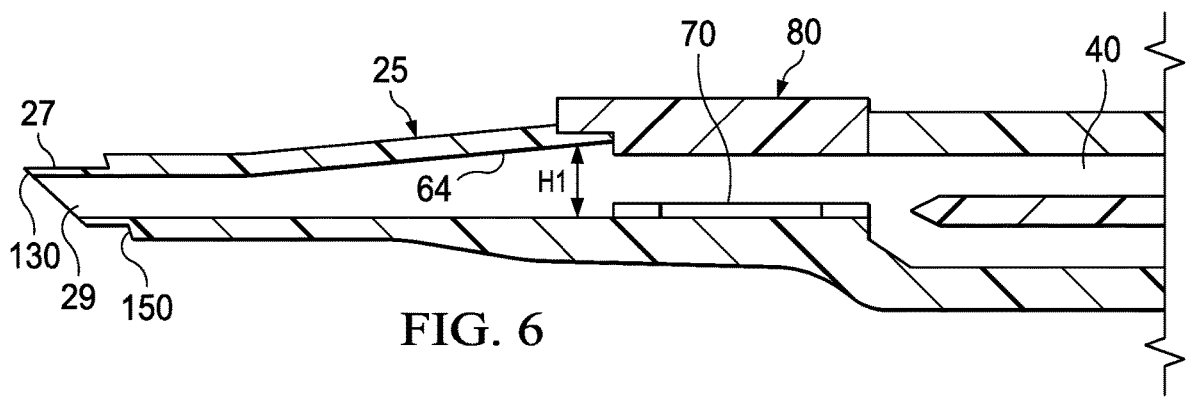
FIG. 6 is a cross-sectional view of the nozzle of the IOL injector of FIG. 5.

In other implementations, the IOL 70 may be a multi-piece IOL, as shown, for example, in FIG. 4. For example, in some implementations, the IOL 70 be include two or more separate components. FIG. 4 is an example IOL 70 that includes two removably attached components. As shown in FIG. 4, the IOL 70 includes an optic 460 and a base 461 that includes haptics 450 and that has a top 498 and a bottom 499. The optic 460 and the base 461 are adapted to be coupled together into a unitary IOL and, thereafter, detached from each other into separate components, if desired. In some instances, one or more components of a multi-piece IOL, such as, for example the two-piece IOL 70 shown in FIG. 4, are separately injectable into a patient's eye. Once in the eye, the components may be assembled into a complete IOL. For example, in the case of the two-piece IOL 70 shown in FIG. 4, the optic 460 and the base 461 are separately injectable into an eye. Once injected, the optic 460 is adapted to be coupled to and to rest on the top 498 of base 461.

Occasionally, patients may require replacement of an IOL, and a procedure to replace an IOL may result in damage to the eye. With the use of a two-piece IOL, for example, a replacement procedure may involve replacement only of the optic, allowing the base to remain in place within the eye.

As explained above, in some implementations, the IOL 70 may be a two-piece IOL wherein the base 461 and the optic 460 are separately injected into the patient's eye. Accordingly, for two-piece IOLs, the base 461 and the optic 460 may be contained in separate IOL injectors 10 for insertion in the eye. In other implementations, the two components of a two-piece IOL may be inserted into an eye separately using a single IOL injector. For a single piece IOL, the optic 460 and haptics 450 form a unitary IOL and are inserted into an eye simultaneously with the use of a single IOL injector.

Accordingly, in some implementations, a user may place a one-piece IOL into an IOL injector, for example, by loading an IOL into the IOL storage compartment of the IOL injector, such as the IOL storage compartment 80 of the IOL injector described above. As also explained, the storage compartment may be accessed via a door, such as the door 90. In some implementations, the IOL may be manually folded into a compressed or folded configuration.

In the case of a two-piece IOL, in some implementations, a user may load the base (which may be similar to base 461) into an IOL storage compartment of an IOL injector, for example, via a door. The optic (which may be similar to optic 460) of may be introduced into the IOL storage compartment of separate IOL injector, for example, via a door. In some instances, the IOL storage compartment may be accessed through the door similar to door 90. In some implementations, one or both of the base and the optic may be manually folded into a compressed or folded configuration.

In some implementations, the IOL may be pre-loaded into the storage compartment of an IOL injector, for example, during manufacturing or otherwise prior to distribution to an end user. Accordingly, for the one-piece IOL, the one-piece IOL may be pre-loaded into the storage compartment an IOL injector prior to receipt by the end user. For a two-piece IOL, the base may be pre-loaded into a storage compartment of one IOL injector, while the optic may be pre-loaded into the IOL storage compartment of another IOL injector. The term "pre-loaded" as used herein means that an IOL, either in a one-piece or multi-piece configuration (including, for example, a two-piece configuration) is loaded into the IOL injector not by a user, but, rather, the IOL is installed in the IOL injector before and is already contained within the IOL injector when the IOL injector is received by the user. The IOL injector(s) may be packaged within sterile packaging when received by a user.

As would be understood by persons of ordinary skill in the art, an IOL that is pre-loaded into an IOL injector has advantages over manual installation and folding of an IOL into the IOL injector that is performed by a user. For example, manual installation and folding of an IOL may allow more opportunity for errors, which have the potential to cause unnecessary secondary manipulation or correction during an already complex procedure. Manual installation and folding of an IOL may also introduce the possibility of contamination of the IOL, such as by human error or poor sterile technique. Contamination of the IOL may compromise the sterile environment for the patient and risk infection or other harm to the patient.

Figure 7:
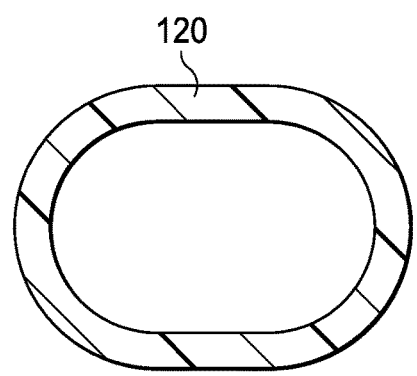
FIG. 7 is an example cross-sectional shape of the nozzle of the IOL injector of FIG. 5.

FIGS. 5-8 illustrate details of the example nozzle 25. In some instances, the nozzle 25 has a tapered exterior surface. Further, the nozzle 25 may include a portion of the bore 40 forming a passage 64 that tapers towards the opening 29. The distal tip 27 is adapted for insertion into an eye so that the IOL 70 may be implanted. The IOL 70 is expelled from the opening 29 formed in the distal tip 27 into the eye. As shown in FIG. 7, the distal tip 27 may have an elliptical cross section 120. Additionally, the distal tip 27 may include a beveled tip 130. The folding device 80, passage 64, and opening 29 may define a delivery passage. A size of the delivery passage may vary along its length. For example, in some instances, a height H1 of the passage may change along a length of the delivery passage. The variation in size of the delivery passage may contribute to the folding of the IOL as it is advanced therealong through the folding device 80.

In some instances, the injector body 20 may include an insertion depth guard 140. The insertion depth guard 140 may form a flanged surface 150 that is adapted to abut an exterior eye surface. The insertion depth guard 140 abuts an eye surface and, thereby, limits an amount by which the distal tip 27 is permitted to extend into an eye, as described in U.S. application Ser. No. 15/049,315, the disclosure of which is being incorporated herein by reference in its entirety.

Figure 8:
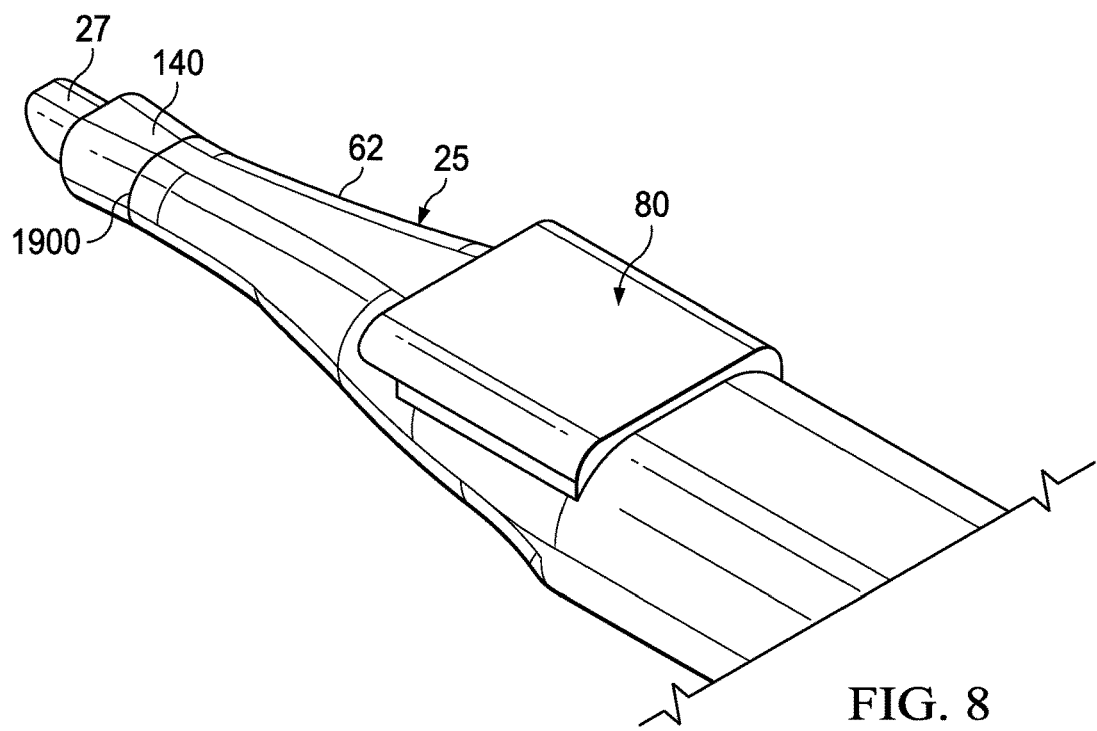
FIG. 8 is another perspective view of the nozzle of the IOL injector of FIG. 5.
Figure 9:
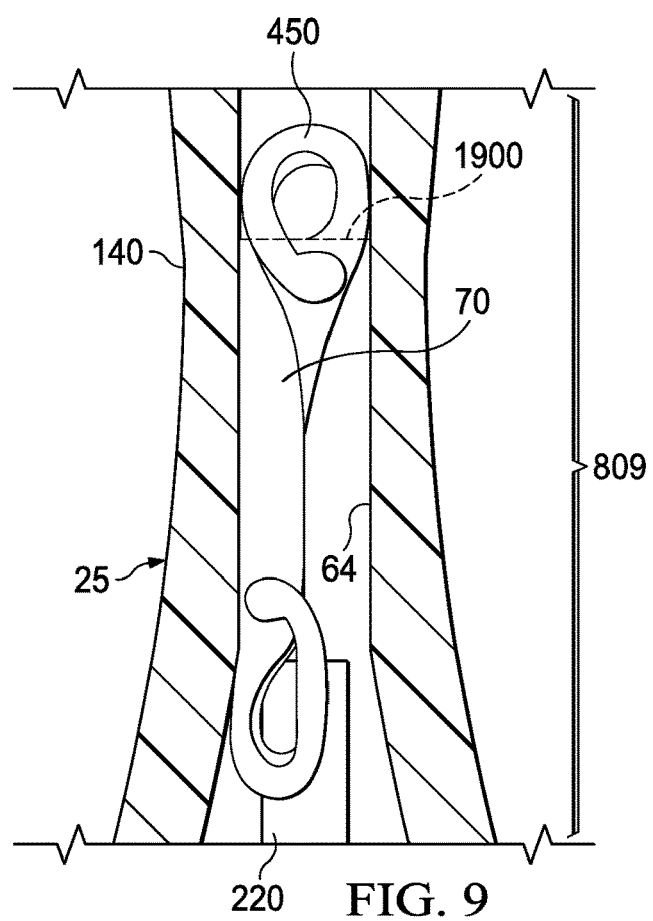
FIG. 9 is a view of a distal end of an IOL injector with an IOL located therein and positioned in a dwell position.

FIG. 8 and FIG. 9 are detail views of a portion of the example nozzle 25. The nozzle 25 may include a tapered portion 62 and the insertion depth guard 140. The distal tip 27 may include a demarcation 1900 that provides a visual indication of a dwell position 809 of the folded or partially folded IOL 70. The term "dwell position" as used herein refers to a location adjacent to the distal end 60 of the nozzle 25. For example, the dwell position 809 may be a location 2-10 mm from the distal end 60. For example, in the example shown in FIG. 8, the demarcation 1900 is a narrow ridge or line that encircles all or a portion of the nozzle 25. In some instances, the demarcation 1900 may be disposed between the tapered portion 62 and the insertion depth guard 140. At least a portion of the injector body 20 may be formed from a transparent or semi-transparent material that permits a user to see an IOL within the injector body 20. Particularly, the nozzle 25 of the injector body 20 may be formed from a transparent material to permit observation of the IOL as it is moved therethrough by the plunger 30.

FIG. 9 shows a view of the distal end 60 of the IOL injector 10 with an IOL 70 located therein at a dwell position 809 in nozzle 25. As shown in FIG. 9, the dwell position 809 of the IOL 70 may be defined as a location where a distal edge of the optic of the IOL 70 substantially aligns with the demarcation 1900. A haptic 450 or a portion thereof may extend beyond the demarcation 1900.

In implementations described herein, the IOL injector 10 may include a collapsible injector body adapted to reduce the length of the IOL injector upon an advancement of the IOL 70 from a storage location, typically in folding device 80, to a dwell position 809.

Figure 10A:
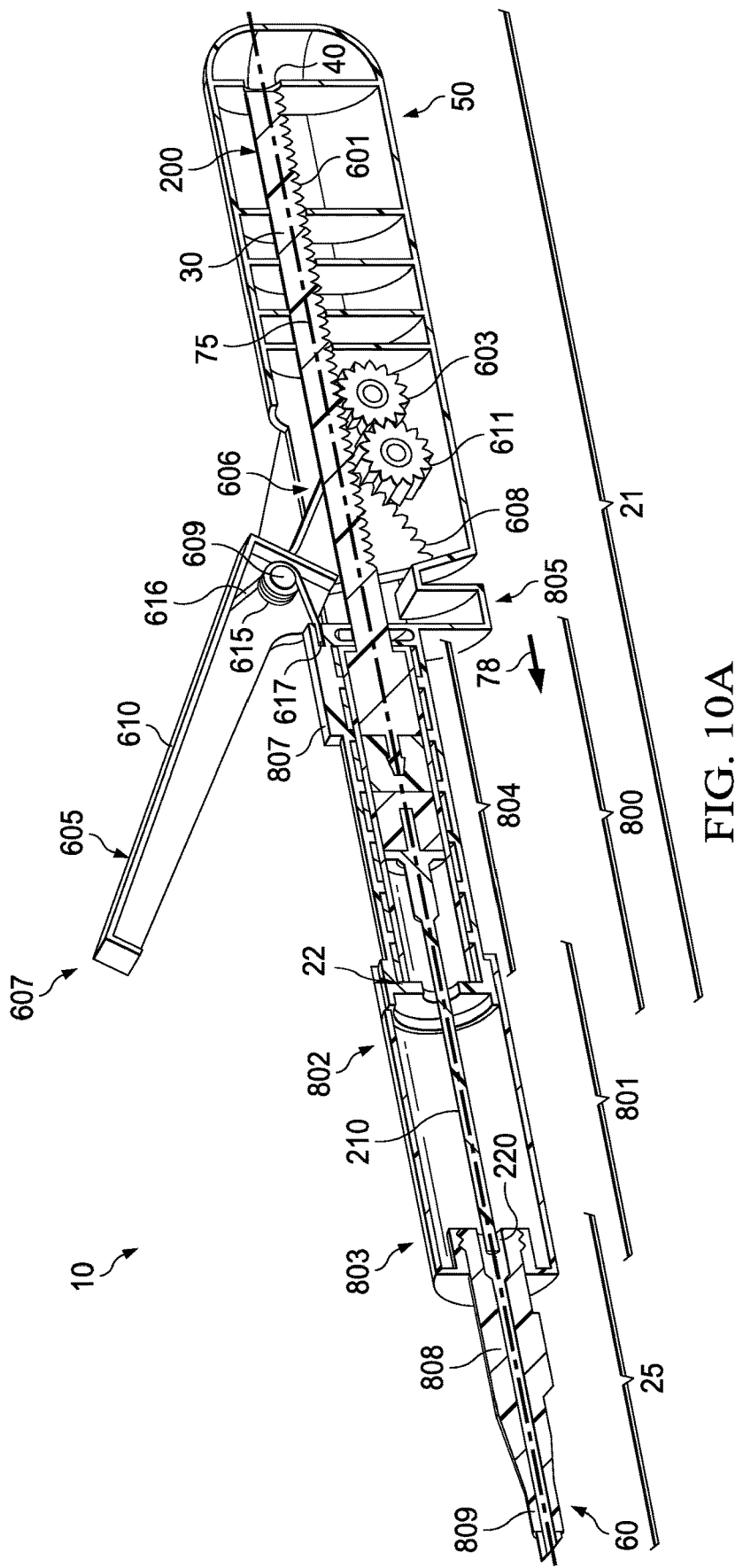
FIG. 10A is a cross-sectional view of an example IOL injector having a collapsible portion of an injector body and a lever-driven rack and pinion system in which the collapsible portion is uncollapsed and a plunger has not been advanced to a distal end of the IOL injector by the lever-driven rack and pinion system.
Figure 10B:
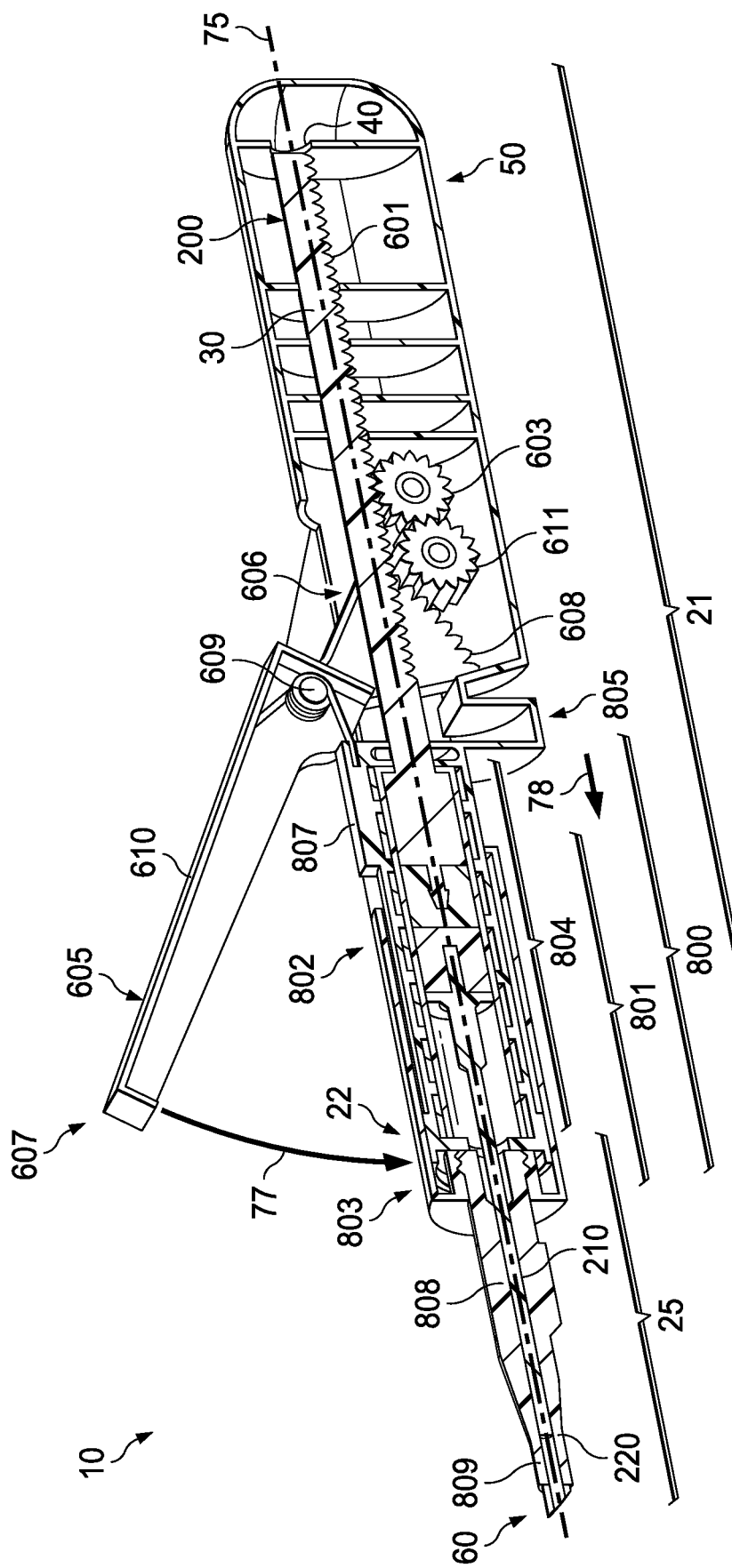
FIG. 10B is another cross-sectional view of the example IOL injector having a collapsible portion of an injector body and a lever-driven rack and pinion system of FIG. 10A, in which the collapsible portion of the injector body has been collapsed and the plunger has not been advanced to the distal end of the IOL injector by the lever-driven rack and pinion system.

FIGS. 10A-10C are a schematic of an example IOL injector 10 wherein the main body 21 includes a collapsible portion 800 that forms a telescoping section, such as a telescoping cylinder.

Although the example IOL injector in FIGS. 10A-10C shows an IOL injector 10 also having a lever-driven rack and pinion system as described herein, the lever-driven rack and pinion system may be absent from an IOL injector 10 having a collapsible portion 800. FIG. 10A shows the IOL injector 10 in the uncollapsed configuration and FIG. 10B shows the same IOL injector 10 in the collapsed configuration.

As would be understood by skilled persons, the term "telescoping" generally refers to movement of a first part sliding out from, or into, a second part, where the two parts are coupled, and have an extended or uncollapsed configuration, and a shortened or collapsed configuration. More specifically, in relation to a "telescoping cylinder" the first and second parts may be tubes or cylinders, herein referred to as "sleeves" of different diameters, wherein a smaller diameter sleeve is coupled concentrically, or nested, within the larger diameter outer sleeve. Two or more concentrically coupled sleeves may be used in a telescoping cylinder. The movement of one sleeve sliding out from, or into another sleeve allows respective lengthening or shortening of the telescoping cylinder. The lengthened, or extended configuration may be referred to as "uncollapsed", and the shortened configuration, for example wherein the length of the smaller diameter tube is entirely or mostly contained within the larger diameter tube may be referred to as "collapsed".

For example, as shown in FIG. 10A, the collapsible portion 800 has at least a first sleeve 801 having a proximal end 802 and a distal end 803. A distal portion of the main body 21 forms a second sleeve 804 having a proximal end 805 and a distal end 22. The proximal end 802 of the first sleeve 801 is slideably coupled with the distal end 22 of the second sleeve 804. In some implementations, for example as shown in FIG. 10A, the distal end 22 of the second sleeve 804 may be slideably coupled concentrically within the proximal end 802 of the first sleeve 801, such that the distal portion of the main body 21 slides concentrically within the proximal end 802 of the first sleeve 801. In other implementations, the first sleeve 801 may be slideably coupled concentrically within the second sleeve 804, such that the first sleeve 801 slides concentrically within the distal portion of the main body 21. In some examples, the first sleeve 801 may slide into a cylindrical space defined between an outer surface of the main body 21 and the bore 40. Other configurations of the collapsible portion are possible.

The first sleeve 801 may be slideably coupled concentrically with the second sleeve 804 using any suitable coupling attachment known to those skilled in the art. For example, the first sleeve 801 and the second sleeve 804 may be slidably coupled by a slip joint adjoining the opposing co-axial surfaces of the first sleeve 801 and the second sleeve 804.

In an uncollapsed configuration, the distal end 22 of the second sleeve 804 is adjacent to the proximal end 802 of the first sleeve 801. In a collapsed configuration, the distal end 22 of the second sleeve 804 is adjacent to the distal end 803 of the first sleeve 801.

The main body 21 may have one or more protrusions 807 on the outer surface of the main body 21, the protrusions 807 placed at the proximal end 805 of the second sleeve 804 and adapted to contact the proximal end 802 of the first sleeve 801 when the collapsible portion 800 is in a collapsed configuration.

In the example IOL injector 10 having a collapsible portion 800 as shown in FIG. 10A, the proximal end of the nozzle 25 is coupled to the distal end 803 of the first sleeve 801. The injector body has a bore 40 having a longitudinal axis 75 extending from the proximal end 50 of the main body 21 to the distal end 60 of the nozzle 25. The IOL injector 10 also has a plunger 30 movably coupled concentrically within the injector body 20 and aligned within the bore 40.

The nozzle 25 has an IOL storage location 808 and an IOL dwell position 809 distal to the IOL storage location 808. In the uncollapsed configuration, the plunger tip 220 has a first position proximally adjacent to the IOL storage location 808. In the collapsed configuration, the plunger tip 220 has a second position proximally adjacent to the IOL dwell position 809. In particular, the plunger tip 220 will typically be 5 to 20 mm proximal to the IOL in the storage location 808 when in an uncollapsed configuration, and the plunger tip 220 will typically be immediately proximally adjacent, in contact and engaged with the trailing, or proximally oriented, haptic of the IOL in the dwell position 809 when in a collapsed configuration.

As described herein, for example, the dwell position 809 position may be indicated by positioning of the IOL, or part thereof, relative to a demarcation. In addition, for example, the dwell position may be indicated by an engagement of the protrusion 807 with the proximal end 802 of the first sleeve 801 when the plunger 30 is in an initial proximal position, prior to an application of an axial force to the plunger 30.

Accordingly, the length of the IOL injector 10 in the collapsed configuration may be 10 to 20% shorter than the length of the IOL injector in the uncollapsed configuration Accordingly, the present disclosure also relates to a method of advancing an IOL 70 from a storage location 808 to a dwell position 809 in an IOL injector 10. The method includes collapsing the collapsible portion by axially sliding the distal end 22 of the second sleeve 804 from the proximal end 802 of the first sleeve 801 to the distal end 803 of the first sleeve 801. As shown in FIG. 10, the sliding is performed in the direction of arrow 78. It will be understood that the method does not involve sliding the plunger 30 in relation to the main body 21, but rather, for example, sliding the main body 21 of the injector body 20 into the first sleeve 801 of the collapsible portion 800 of the main body 21. Accordingly, in collapsing the injector body in this way, the plunger 30 does not move, or does not substantially move, in relation to the second sleeve 801. In addition, collapsing the IOL injector 10 in this way results in a shorter IOL injector 10 for use in injecting the IOL into the eye from the dwell position 809. The collapsible feature improves ergonomics by reducing the overall length of the IOL injector 10.

FIG. 10B shows the IOL injector 10 in the collapsed configuration after sliding the second sleeve 804 into the first sleeve 801 of the collapsible portion 800 of the injector body 20. In the collapsed configuration, for example as shown in FIG. 10B, the distal end 22 of the second sleeve 804 is adjacent to the distal end 803 of the first sleeve 801, the protrusion 807 on the main body 21 is in contact with the proximal end 802 of the first sleeve 801, and the plunger tip 220 is in the second position proximally adjacent to the IOL dwell position 809.

Due to the sensitivity and delicacy of ocular tissues and structures, it will be understood by skilled persons that it is important that the user is able to advance the IOL with acceptable peak speed and force. Inherent to the mechanism of some existing IOL injectors, when folding and advancing the IOL into the eye, there is typically a high peak axial force and a large pressure release when the IOL passes through the exit of the distal tip, in some cases this causes the IOL to be ejected with high velocity in a less controllable manner. Some existing IOL injectors include a spring, whose elevated force is felt by the user throughout the delivery. Higher peak forces such as these have been characterized by some users as being too high for them to use the device consistently and comfortably. These pressure and force hikes and troughs reduce user control of the IOL injector and ultimately the IOL delivery. The challenges of delivering the IOL include ensuring that the mechanism and magnitude of force applied through user interaction is appropriate and repeatable. It is also important to have a IOL injector that is intuitive and can be utilized by users of the entire spectrum of skills and techniques.

The present disclosure also relates to an IOL injector having a lever-driven rack and pinion system adapted to actuate an axial movement of a plunger in response to a lever press.

As would be understood by skilled persons, a rack and pinion is a type of linear actuator that includes a pair of gears which convert rotational motion into linear motion. A circular gear called the "pinion" engages teeth on a linear gear bar called the "rack". Rotational force applied to the pinion causes the rack to move relative to the pinion, thereby translating the rotational movement of the pinion into linear movement of the rack.

For example, FIGS. 10A-10C are schematics of an example IOL injector 10 having a lever-driven rack and pinion system. In FIGS. 10A-10B, the plunger 30 has not been advanced to distal end 60 by the lever-driven rack and pinion system. In FIG. 10C, the plunger 30 has been advanced to distal end 60 by the lever-driven rack and pinion system. Although the example IOL injector in FIGS. 10A-10C shows an IOL injector 10 also having a collapsible portion 800, the collapsible portion 800 may be absent from an IOL injector 10 having the lever-driven rack and pinion system. FIG. 11, FIG. 12, and FIGS. 16A-16C are also schematics showing various views of example IOL injectors having various implementations of the lever-driven rack and pinion system.

In FIGS. 10A-10C, 11 and 12, the plunger body 200 of the plunger 30 has a plunger rack 601 including a plurality of teeth 602. The IOL injector 10 also has a first pinion 603 having a plurality of teeth 604 adapted to interface, or mesh, with the teeth 602 of the plunger rack 601, such that the plunger rack 601 is linearly movable in response to rotational movement of the first pinion 603. The IOL injector 10 also has a second pinion 611 having a plurality of teeth 612 adapted to interface with the teeth 604 of the first pinion 603. The IOL injector 10 also has a lever 605 having a proximal end 606 and a distal end 607, the lever having an arcuate rack 608 at the proximal end 606 of the lever 605. The arcuate rack 608 has a plurality of teeth 619 adapted to interface with the teeth 612 of the second pinion 611, such that the second pinion 611 is rotationally movable in response to movement of the arcuate rack 608.

The lever 605 has a pivot point 609 located between the proximal end 606 of the lever 605 and the distal end 607 of the lever 605, the pivot point 609 rotatably coupled to the injector body 20 and adapted to allow a rotational movement of the lever 605 about the pivot point 609. The lever has a depressible surface 610 accessible to a user, the depressible surface 610 located between the pivot point 609 and the distal end 607 of the lever 605. In response to a depression of the depressible surface 610 of the lever 605, the lever 605 is adapted to rotate about the pivot point 609 in a first rotational direction as indicated by the arrow 77, the second pinion 611 is adapted to rotate in a second rotational direction opposite the first rotational direction, and the first pinion is adapted to rotate in the first rotations direction so that the plunger rack 601 is advanced in a linear direction indicated by arrow 78 towards the distal end 60 of the IOL injector 10.

In some implementations, only a single pinion may be present, in which case, the lever 605 may be in an opposite axial orientation to that shown in FIGS. 10A-10C.

In some implementations, the plunger rack and pinion may include more than two pinions rotatably coupled such that an axial movement of the plunger 30 is actuated in response to a depression of the lever 605. The lever 605 may have an axial orientation suitable to achieve the desired axial movement of the plunger 30.

In some implementations, for example as shown in FIG. 10A, the lever-driven rack and pinion system may further include a reset spring 615 having a first end 616 coupled to the lever 605 and a second end 617 coupled to the main body 21, the reset spring 615 adapted to rotate the lever in a second rotational direction. In some implementations, such as shown in FIG. 10A, the reset spring may be a torsion spring.

Figure 12:
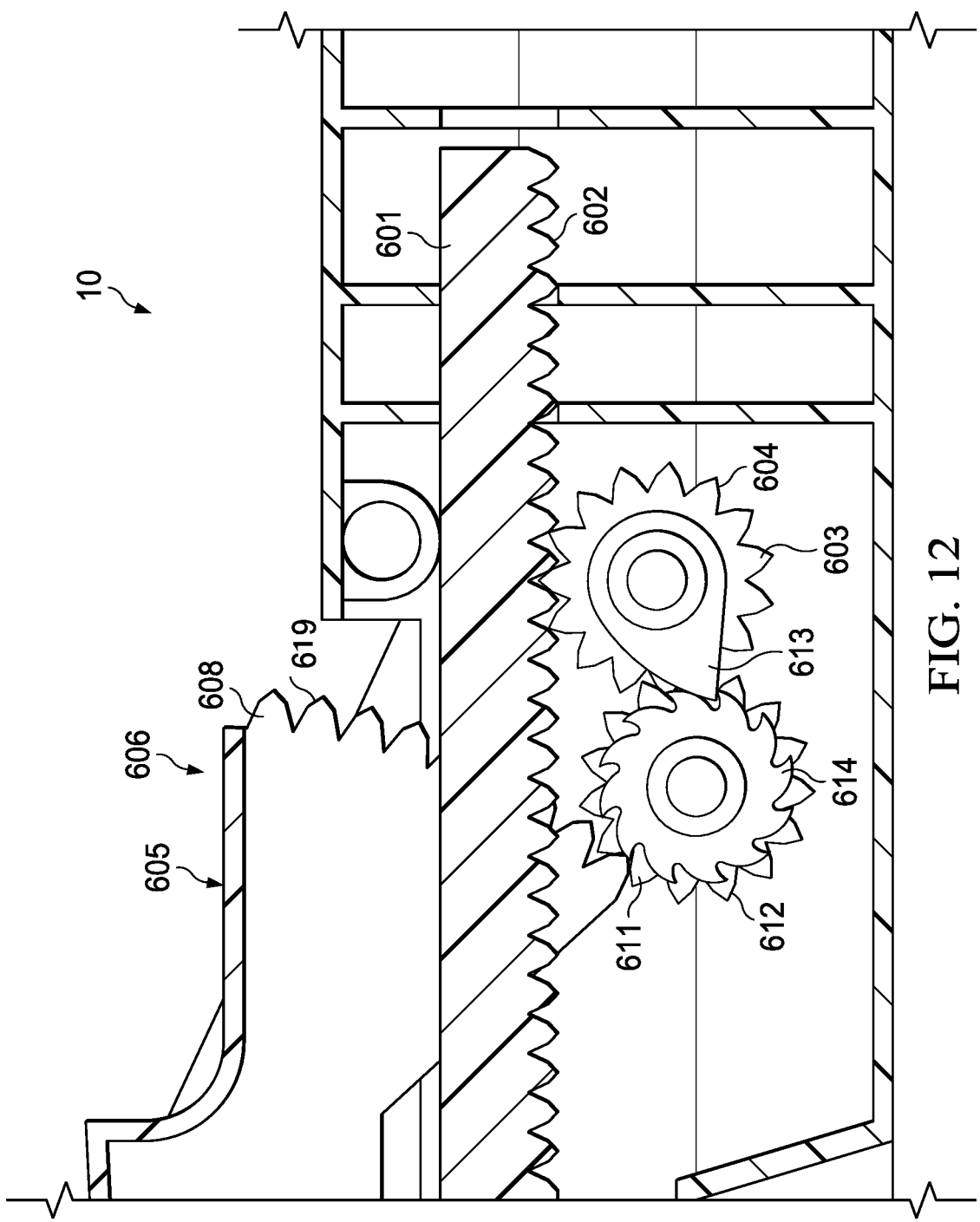
FIG. 12 is a cross-sectional view of the rack and pinion portion of an example IOL injector having a lever-driven rack and pinion system.

In some implementations, the lever-driven rack and pinion system may further include a one-way gear system, for example as shown in FIG. 12, wherein the first pinion 603 further includes a rotary pawl 613, the second pinion further includes a rotary ratchet 614. The rotary pawl 613 is adapted to interface with the rotary ratchet 614 to prevent movement of the plunger body 200 of the plunger 30 toward the proximal end 50 of the injector body 20. Accordingly, the example rotary ratchet 614 and pawl 613 system shown in FIG. 12 allows actuation reset of the lever 605 to be decoupled from movement of the plunger 30. In other words, the one-way gear system allows rotation of the lever in a second rotational direction, e.g. by the return spring 615, to be decoupled from actuating movement of the plunger rack 601, thereby preventing retraction of the plunger 30 toward the proximal end 50 of the injector body 20.

In some implementations, the present disclosure relates to an IOL injector having a slide advance and lever-driven rack and pinion injection mechanism. Accordingly, in some implementations, the IOL injector 10 described herein is adapted to advance the IOL from the storage location 808 to the dwell position 809 by the user axially sliding the plunger 30 actuated by applying an axial force to a flange 240. Upon advancing the IOL to the dwell position 809, a lever-driven rack and pinion mechanism is engaged that is adapted to allow advancement of the IOL axially from the dwell position 809 and into the patient's eye.

Figure 16A:
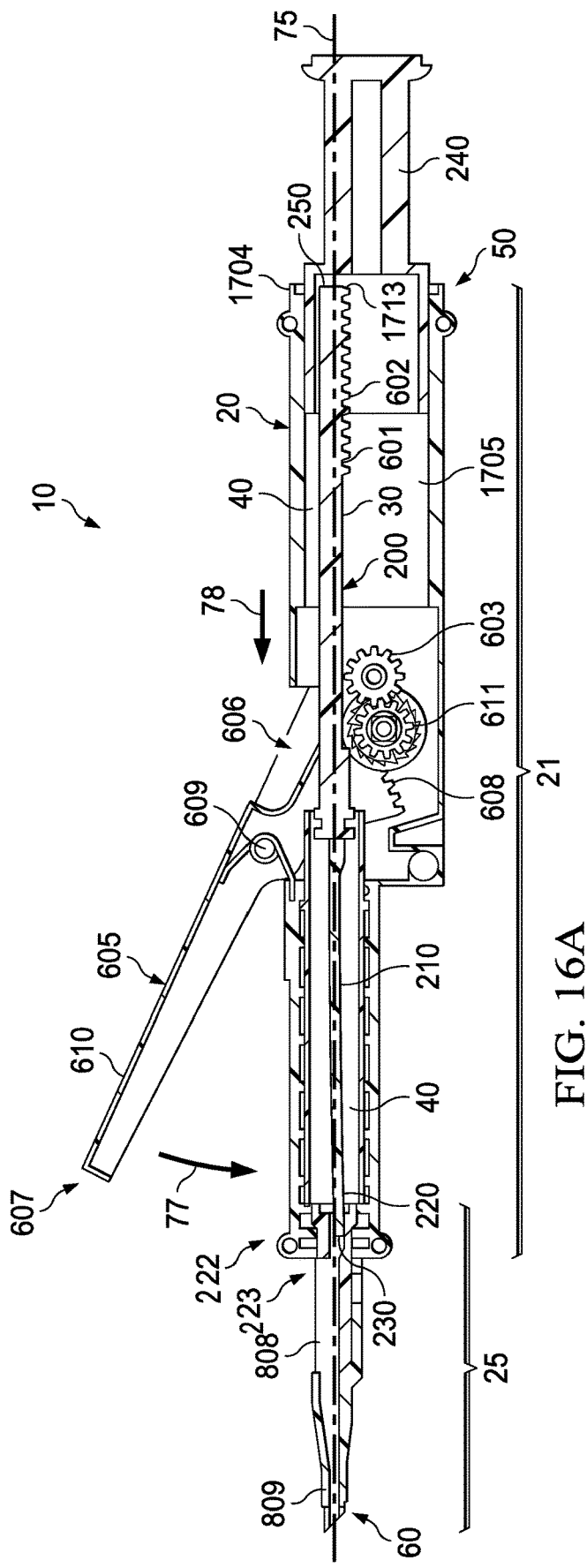
FIG. 16A is a schematic showing an implementation of an IOL injector having a slide advance to dwell and a lever-driven rack and pinion mechanism.
Figure 16B:
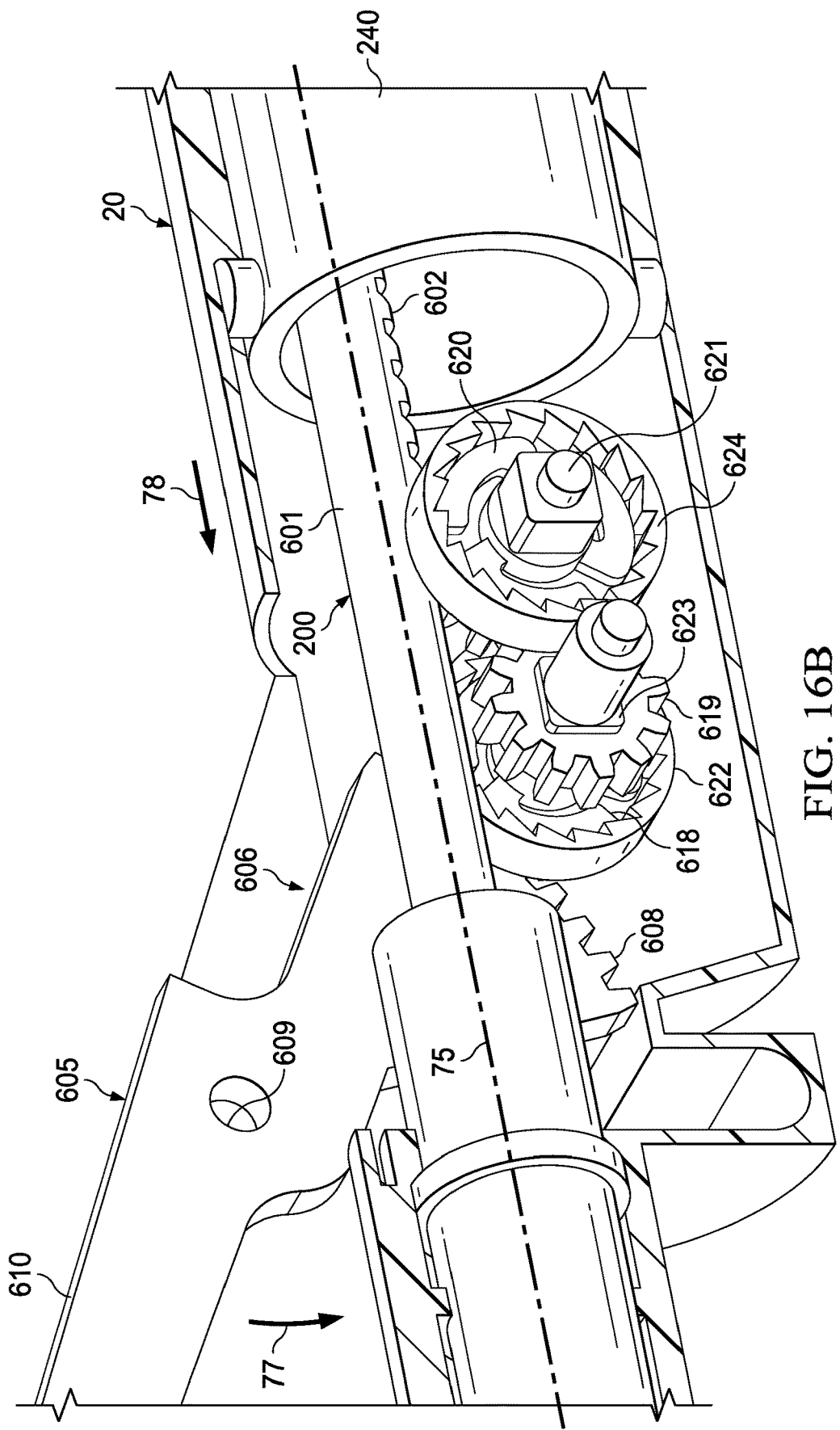
FIG. 16B is a detail view of an example one-way gear system of the IOL injector having the lever-driven rack and pinion mechanism of FIG. 16A.
Figure 16C:
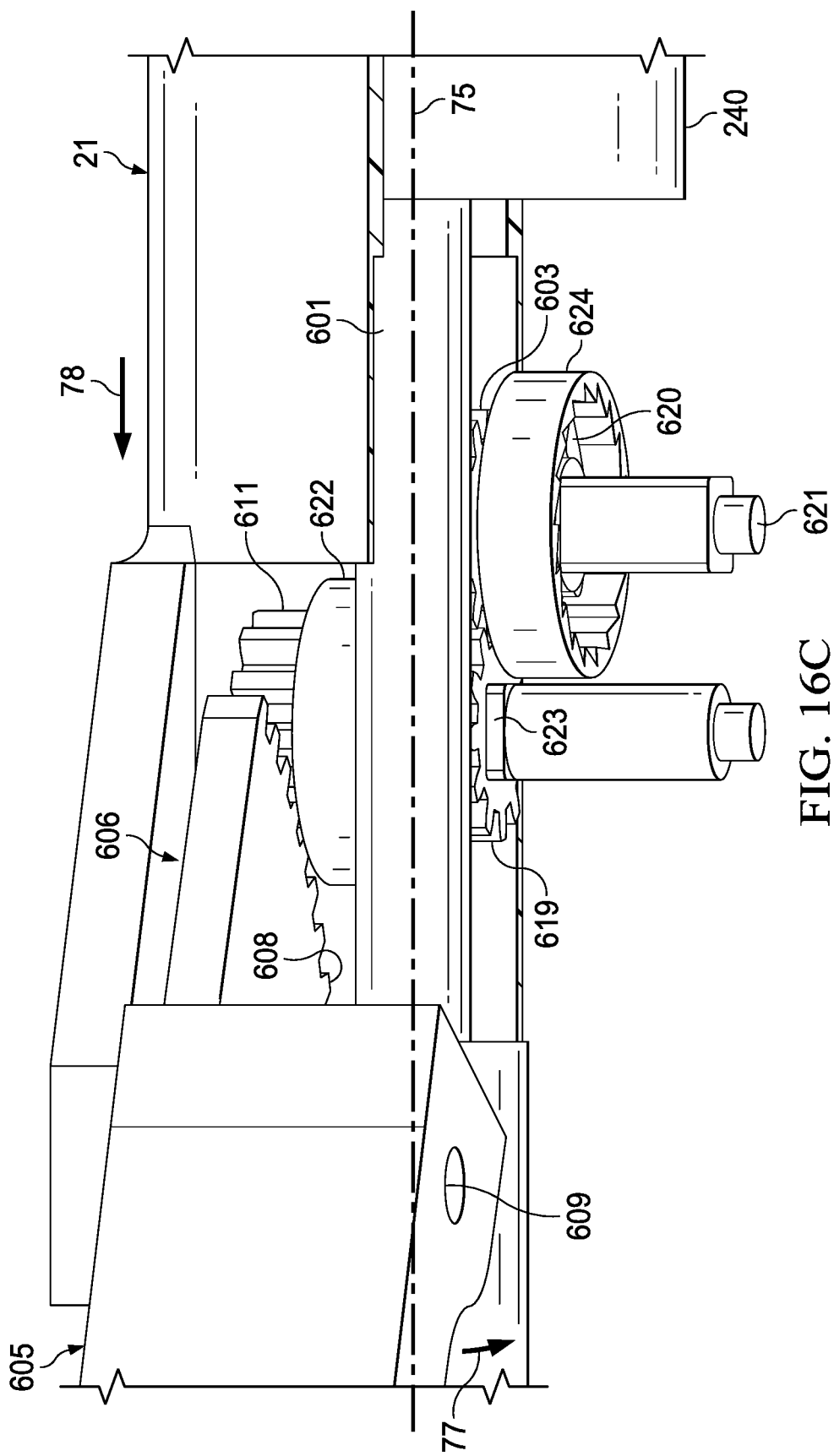
FIG. 16C is another detail view of an example one-way gear system of the IOL injector having the lever-driven rack and pinion mechanism of FIG. 16A.

FIGS. 16A-16C show an example implementation of the IOL injector 10 having a slide advance and lever-driven rack and pinion injection mechanism. The IOL injector 10 having the slide advance and rack and pinion injection mechanism has an injector body 20. The injector body 20 includes a main body 21 having a proximal end 222 and a distal end 50. The injector body 20 also includes a nozzle 25 having a proximal end 23 and a distal end 60, the proximal end 223 of the nozzle 25 coupled to the distal end 222 of the main body 21. The injector body 20 has a bore 40 having a longitudinal axis 75 from a proximal end 50 of the main body 21 to the distal end 60 of the nozzle 25. The IOL injector 10 also has a plunger 30 movably coupled within the injector body 20 and aligned with the bore 40. The plunger 30 has a plunger body 200 having a proximal end 250 and a distal end 230 and a plunger rack 601 including a plurality of teeth 602. The plunger 30 also has a plunger rod 210 having a proximal end and a distal end 230, the proximal end of the plunger rod 210 coupled to the distal end of the plunger body 200. The plunger rod has a plunger tip 220 adapted to contact an IOL, the plunger tip 220 formed at the distal end 230 of the plunger rod 210.

The example IOL injector 10 shown in FIGS. 16A-16C also has a first pinion 603 having a plurality of teeth adapted to interface, or mesh, with the teeth 602 of the plunger rack 601, wherein the plunger rack 601 is linearly movable in response to rotational movement of the first pinion 603. The IOL injector 10 also has a lever 605 having a proximal end 606 and a distal end 607, the lever having an arcuate rack 608 at the proximal end 606 of the lever 605. In some implementations, the arcuate rack 608 may have a plurality of teeth adapted to interface with the teeth of the first pinion 603, wherein the first pinion 603 is rotationally movable in response to movement of the arcuate rack 608. The lever 605 has a pivot point 609 located between the proximal end 606 of the lever 605 and the distal end 607 of the lever 605, the pivot point 609 rotatably coupled to the injector body 20 and adapted to allow a rotational movement of the lever 605 about the pivot point 609. The lever has a depressible surface 610 accessible to a user, the depressible surface 610 located between the pivot point 609 and the distal end 607 of the lever 605. In response to a depression of the depressible surface 610 of the lever 605, the lever 605 is adapted to rotate about the pivot point 609 in a first rotational direction as indicated by the arrow 77, the first pinion 603 is adapted to rotate in a second rotational direction; and the plunger rack 601 is adapted to move in a first linear direction indicated by arrow 78 towards the distal end 60 of the nozzle 25.

In some implementations, such as shown in FIG. 16A, the lever-driven rack and pinion system may further include a second pinion 611 having a plurality of teeth adapted to interface with the teeth of the arcuate rack 608 and the teeth of the first pinion 603, wherein in response to the depression of the depressible surface 610 of the lever 605, the lever 605 is adapted to rotate about the pivot point 609 in a first rotational direction as shown by the arrow 77, the second pinion 611 is adapted to rotate in a second rotational direction opposite that shown by the arrow 77, the first pinion 603 is adapted to rotate in a first rotational direction shown by the arrow 77; and the plunger rack 601 is adapted to move in a first linear direction indicated by arrow 78 towards the distal end 60 of the nozzle 25.

In the example IOL injector shown in FIG. 16A, a flange 240 is adapted to contact the plunger body 200. For example, the flange may be adapted to contact the proximal end 250 of the plunger body 200. The flange 240 is adapted to move axially within the main body 21 in response to an axial force applied in the direction of the arrow 78. Accordingly, the plunger body 200 is adapted to move axially in response to movement of the flange 240. The IOL injector 10 may also include a channel 1705 adapted to allow axial movement of the flange 240 in response to an axial force applied to the flange 240.

In particular, for example as shown in FIG. 16A, the channel 1705 may be an opening at the distal end 50 of the main body 21 adapted to allow axial movement of the plunger 30 in response to an axial force applied to the flange 240, wherein the plunger 30 is slidably disposed within the channel 1705 and the flange 240 is accessible to a user.

The plunger 30 is movable in response to an axial force applied to the flange 240. This moves the IOL from a storage location to a dwell position. The first pinion 603 is rotatably coupled with the plunger rack 601 and the plunger 30 is axially movable in response to a depression of the lever 605 actuating rotation of the first pinion 603. This moves the IOL from the dwell position 809 into the eye.

In some implementations, as shown in FIG. 16A, the plunger tip 220 is movable from a first position proximally adjacent to the IOL storage location 808 to a second position proximally adjacent to the IOL dwell position 809 in response to an axial force applied to the flange 240 in a first direction indicated by the arrow 78, and the plunger tip 220 is movable from the second position to the distal end 60 of the nozzle 25 in response to depression of the lever 605 in a first rotational direction indicated by the arrow 77.

In particular, the plunger tip 220 will typically be 5 to 20 mm proximal to the IOL in the storage location 808 when in the first position, and the plunger tip 200 will typically be immediately proximally adjacent, in contact and engaged with the trailing, or proximally oriented, haptic of the IOL in the dwell position 809 when in the second position.

In some implementations, the IOL injector 10 may include a hard stop mechanism, having a barrier 1704 adapted to prevent movement of the flange 240 in a first axial direction indicated by the arrow 78 toward the distal end 60 of the nozzle 25. In particular, the barrier 1704 may be adapted to prevent movement of the flange 240 in a first axial direction indicated by the arrow 78 toward the distal end 60 of the nozzle 25 upon axial advancement of the plunger tip 220 to the second position proximally adjacent to the dwell position 809. For example, the barrier 1704 may be adapted to contact the flange 240, upon movement of the plunger tip 220 to the second position proximally adjacent to the dwell position 809, thereby preventing movement of the plunger 30 in a first axial direction indicated by the arrow 78 toward the distal end 60 of the nozzle 25. Accordingly, the hard stop mechanism is adapted to decouple the movement of the plunger tip 220 from the first position proximally adjacent to the IOL storage location 808 to the second position proximally adjacent to the dwell position 809 in response to an axial push of the flange 240, from movement of the plunger tip 220 from the second position proximally adjacent to the IOL dwell position 809 toward the distal end 60 of the nozzle 25 in response to depression of the lever 605.

In some implementations, the flange 240 may be detachable, or adapted to be decoupled, from the plunger body 200 of the plunger 30, for example at a detaching point 1713. In some implementations, the flange 240 and a proximal portion of the plunger body 200 may be detachable from a distal portion of the plunger body 200 at the detachment point 1713, wherein the distal portion of the plunger 30 includes the plunger rack 601. Accordingly, in various implementations, the detachment point 1713 allows detachment of a proximal portion of the plunger 30 that is slideable within the bore 40 upon application of an axial force applied to the flange 240 from a distal portion of the plunger 30 having the plunger rack 1703 that is movable in the direction of arrow 78 in response to a depression of the lever 605. Detachment at the detachment point 1713 of the proximal portion of the plunger 30 from the distal portion of the plunger 30 is adapted in some implementations to allow advancement of the distal portion of the plunger 30 in response to the depression of the lever 605, allowing the plunger tip 220 to move from the second position proximally adjacent to the dwell position 809 to the distal end 60 of the nozzle 25. For example, the cross-section schematic shown in FIG. 16A shows an example IOL injector 10 in a configuration prior to sliding the plunger in the direction of arrow 78 upon application of an axial force to the flange 240. In FIG. 16A, for example, the plunger tip 220 is in a first position proximally adjacent to the storage location 808.

Details of another example implementation of a one-way gear system is shown in FIGS. 16B and 16C.

The example one-way gear system shown in FIGS. 16B and 16C is adapted such that depression of the lever 605 in the direction of the arrow 77 rotates the second pinion 611. The second pinion is fixedly coupled to a first circular ratchet 622. In response, a first pawl 618 is engaged with the first circular ratchet 622, which turns a one-way gear 619, which is fixedly coupled to the first pawl 618 by a first axle 623. The first pawl 618 is concentrically disposed within and adapted to rotatably mesh with the first circular ratchet 622. In response, the first gear 619 meshes with and rotates the first pinion 603. A second pawl 620 is non-rotationally fixed, or fixedly coupled, to the injector body 20 by a second axle 621. The term non-rotationally fixed means that the second pawl 620 is adapted not to rotate, but rather the second circular ratchet 624 is adapted to rotate about the second pawl 620. The second pawl 620 is concentrically disposed within and adapted to rotatably mesh with the second circular ratchet 624. Accordingly, the second circular ratchet 624 is adapted to slip within a second circular ratchet 624 that is fixedly coupled to the first pinion 603, allowing the plunger rack 601 to advance in the direction of the arrow 78, thereby axially advancing the plunger body 200 and thereby advancing the IOL from the dwell position to be delivered into an eye of a patient.

Upon lever 605 reset, for example, when actuated by a return spring, when the lever 605 is rotated in a second rotational direction opposite to the rotational direction of the arrow 77, the plunger rack 601 is prevented from moving towards the proximal end of the main body 21 of the injector body 20 by the second circular ratchet 624, which is adapted to catch on the rotationally fixed second pawl 620. Accordingly, the one-way gear 619 is prevented from rotating by the first pinion 603. The first circular ratchet 622 is adapted to slip along the first pawl 608, thereby allowing the lever 605 to move in a second rotational direction opposite to the rotational direction of the arrow 77 without advancing the plunger 30.

Figure 13A:
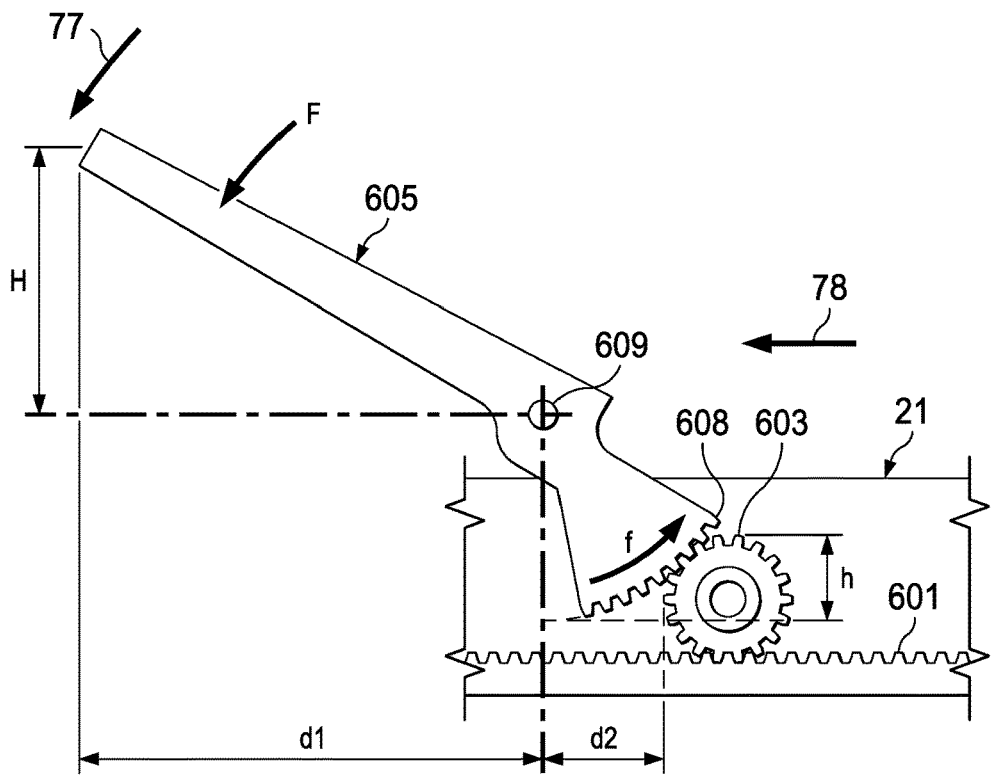
FIG. 13A is a schematic of an example lever-driven rack and pinion system.
Figure 13B:
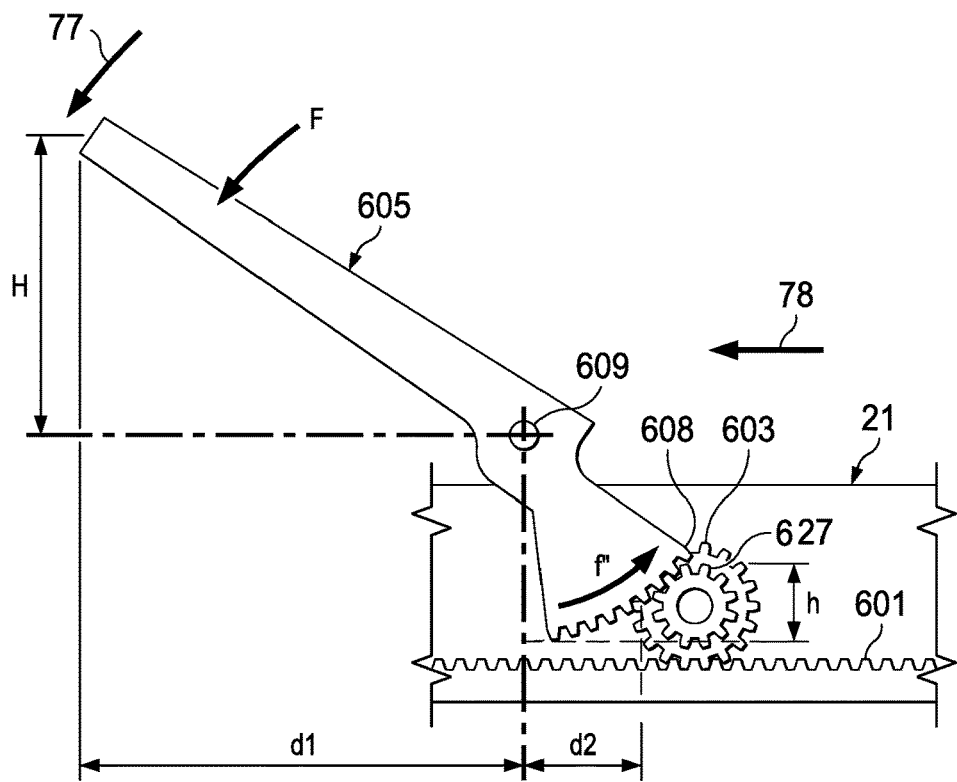
FIG. 13B is another schematic of an example lever-driven rack and pinion system.

FIG. 13A and FIG. 13B are schematics of an example lever-driven rack and pinion system. In particular, FIG. 13A and FIG. 13B illustrate example parameters relating to the lever-driven rack and pinion system herein described, wherein F is a force applied to depress the lever 605, f is the force to rotate a pinion, such as a first pinion 603 rotatably coupled with the arcuate rack 608 in response to movement of the arcuate rack 608, wherein the first pinion has a circumference $R_1$ having a value. The distal end of the lever 605 has a rotational distance H which is a distance of rotation measured from an outer surface of the injector body 20, wherein H has a maximal value in absence of a lever depression force F and the value of H is minimal when the lever 605 is fully depressed. The proximal end of the lever 605 has a movement distance h of the arcuate rack 608, wherein h has a value that varies inversely with the value of H. The plunger rack 601 has a length r equal to the distance of the movement of the IOL from the dwell position 809 into the patient's eye. The lever 605 has a distance $d_1$ from the pivot point 609 to the distal end 607 of the lever 605 and a distance $d_2$ from the pivot point 609 to the arcuate rack 608.

In various implementations of the lever-driven rack and pinion system described herein, varying the values of the parameters of the system may provide variation in gaining mechanical advantage through leverage on the force F required to depress the lever 605 to actuate axial movement of plunger rack 601, and/or the number of depressions of the lever 605 that are required to actuate axial movement of the plunger rack 601 the distance r. For example, in the example lever-driven rack and pinion system of FIG. 13A, the following example parameter values may apply: H=15 mm, h=6 mm, $d_1$=25 mm, $d_2$=10 mm, $R_1$=5-6 mm and r=35 mm. Accordingly, applying such example values gives F/f≈2/5, providing a reduction in force required to depress the lever to actuate a movement of the plunger 30 in response. In the example shown in FIG. 13A, $r/R_1$≈6, such that approximately 6 depressions of the lever 605 are required to actuate movement of the plunger rack 601 the distance r.

In other implementations, for example as shown in FIG. 13B, to reduce the number of depressions of lever 605 that are required to actuate movement of the plunger rack 601 the distance r, a second pinion 627 may be included together with the first pinion 603 to form a gear set, such as a compound gear, also known as a concentric gear, or a double gear such as shown in FIG. 13B, among others identifiable by skilled persons upon reading the present disclosure. In the example gear set as shown in FIG. 13B, the arcuate rack 608 is rotatably coupled with the first pinion 603 wherein the teeth 609 of the arcuate rack 608 are adapted to rotatably interface with the teeth of the first pinion 603. The second pinion 627 may be fixedly coupled with the first pinion 603 such that the first pinion 603 and the second pinion 611 share a rotational center, so that one rotation of the first pinion 603 is fixedly coupled with one rotation of the second pinion 611. Accordingly, the second pinion 627 may have a circumference $R_2$ having a value. In some implementations, the ratio of the values of $R_2$ to $R_1$ may be from 1:1 to 1:5. Accordingly, the ratio of the value of $R_2$ to $R_1$ may provide a mechanical advantage. For example, as shown in FIG. 13B, the following parameter values may apply: $R_1$=5-6 mm, $R_2$=24 mm, giving a ratio of $R_2$ to $R_1$ of about 1:4 to 1:5. Skilled persons will understand that a gear ratio such as in the example shown in FIG. 13B may reduce the mechanical advantage of the lever in reducing the force F required to be applied to the lever 605. For example, the a force f" required to rotatably move the smaller second pinion 627 in the gear set depicted may be decreased compared to the force required to rotatably move the larger first pinion 603. In another example (not shown), the a force f" required to rotatably move the larger second pinion in such a gear set may be increased compared to the force required to rotatably move the smaller first pinion. For example, the following example parameters may apply: d1=30 mm, d2=5 mm, H=24 mm, h=4 mm, such that f"/f=5, F/f"=1/6, thus F/f=5/6, giving 20% reduction in force required to depress the lever 605. In addition, such parameters will reduce the number of depressions of the lever 605 such that one depression of the lever 605 actuates an axial advancement of the plunger rack 24 mm. For a plunger rack having distance r=40 mm, such a gear set allows axial movement of the plunger rack a distance r with two depressions of the lever 605, which is preferable to approximately 6 depressions of the lever 605 being required to actuate movement of the plunger rack 601 the distance r.

Accordingly, in some implementations, the lever-driven rack and pinion system may be adapted to move the plunger rack 601 a distance of length r in response to 1 to 10 depressions of the lever 605.

As would be understood by skilled persons, in various implementations, the values of $R_1$ and $R_2$ may be optimized by skilled persons so as to provide a suitable balance of force F required to depress the lever 605 and the number of depressions of the lever 605 that are required to actuate movement of the plunger rack 601 the distance r.

In some implementations, the IOL injector 10 may also include a ribbed damping mechanism adapted to provide a frictional resistance to the axial force.

Figure 14:
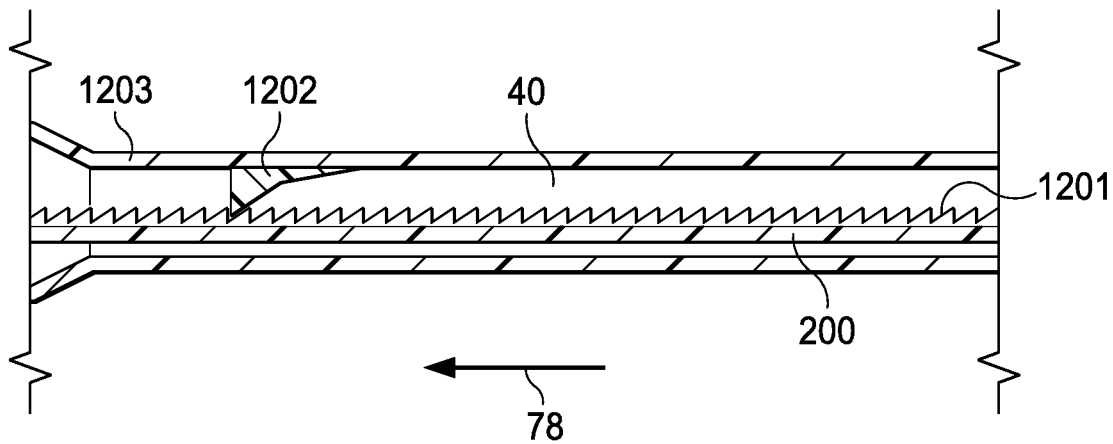
FIG. 14 is a detail view of an example ribbed damping system.

FIG. 14 is a detail view of an example ribbed damping system. In the main body, the bore 40 may also include a ribbed damping mechanism adapted to provide a frictional resistance to the axial force. The ribbed damping mechanism includes at least one rib 1201 on the plunger body 200 and at least one rib 1202 on an interior wall 1203 of the bore 40, wherein the at least one rib 1201 on the plunger body 200 is adapted to contact the at least one rib 1202 on the interior wall 1203 and adapted to provide a frictional resistance to the axial movement of the plunger 30. The ribbed damping mechanism may be composed of flexible material, such as deformable plastic, such that contact between the ribs 1201 and 1202 during the axial movement of the plunger 30 causes resistance to the axial movement in the direction of arrow 78 but does not prevent axial movement in the direction of arrow 78.

As shown in FIG. 14, in some implementations, one or more of the ribs 1201 on the plunger body 200 of the plunger 30 may form a ridge and one or more ribs 1202 on the interior wall 1203 may form a ridge-engaging tooth, wherein the ridge and the ridge-engaging tooth are adapted to prevent movement of the distal end 220 of the plunger 30 in a second axial direction, toward the proximal end of the main body of the IOL injector. For example, the ribs 1201 on the plunger body 200 of the plunger 30 may form a ratchet, and the one or more ribs 1202 on the interior wall 1203 may form a pawl.

In other implementations, one or more of the ribs 1201 on the interior wall 1203 may form a ridge and one or more ribs 1202 on the plunger body 200 of the plunger 30 may form a ridge-engaging tooth, wherein the ridge and the ridge-engaging tooth are adapted to prevent movement of the distal end 220 of the plunger 30 in a second axial direction, toward the proximal end of the main body of the IOL injector. For example, the ribs 1202 on the interior wall 1203 may form a ratchet, and the one or more ribs 1201 on the plunger body 200 of the plunger 30 may form a pawl.

In some implementations, the one or more ribs 1201 and/or 1202 may be a plurality of ribs 1201 and/or 1202, and the distance between each of the ribs 1201 and/or 1202 may decrease with decreasing distance from the distal end of the main body. Accordingly, having a closer placement of the ribs 1201 and/or 1202 toward the distal end of the main body 200 and/or interior wall 1203 of the bore 40 may provide increased resistance to counteract the typically high peak axial force and the large pressure release when the IOL passes through the exit of the distal tip.

In any of the implementations described herein, the components of the IOL injectors may be combined with one another. For example, the IOL injector having the lever-driven rack and pinion system may further include the ribbed damping mechanism. The injector body having the lever-driven rack and pinion system and/or the ribbed damping mechanism may include the collapsible portion, wherein the main body has a proximal end and a distal end, a collapsible portion forming a telescoping cylinder having at least two sleeves, wherein a first sleeve has a proximal end and a distal end, and a distal portion of the main body forms a second sleeve having a proximal end and a distal end, wherein the first sleeve is slideably coupled with the second sleeve, and an nozzle having a proximal end and a distal end, wherein the proximal end of the nozzle is coupled to the distal end of the first sleeve of the collapsible portion.

Accordingly, in some implementations wherein the IOL injector 10 includes the lever-driven rack and pinion system and the collapsible portion, the IOL injector may be adapted so that the teeth of the plunger rack contact the teeth of the first pinion when the plunger when the IOL injector is in the collapsed configuration but not in the uncollapsed configuration. Accordingly, the plunger body 200 of the plunger 30 may have a distal portion that does not have a plunger rack 601 including teeth 602 adapted to contact the first pinion 603 or the second pinion 611, such that the distal portion of the plunger body 200 is adapted to freely move axially together with the main body 21 of the injector body 20 during the collapsing the collapsible portion 800, without engaging the lever-driven rack and pinion system.

Figure 15:
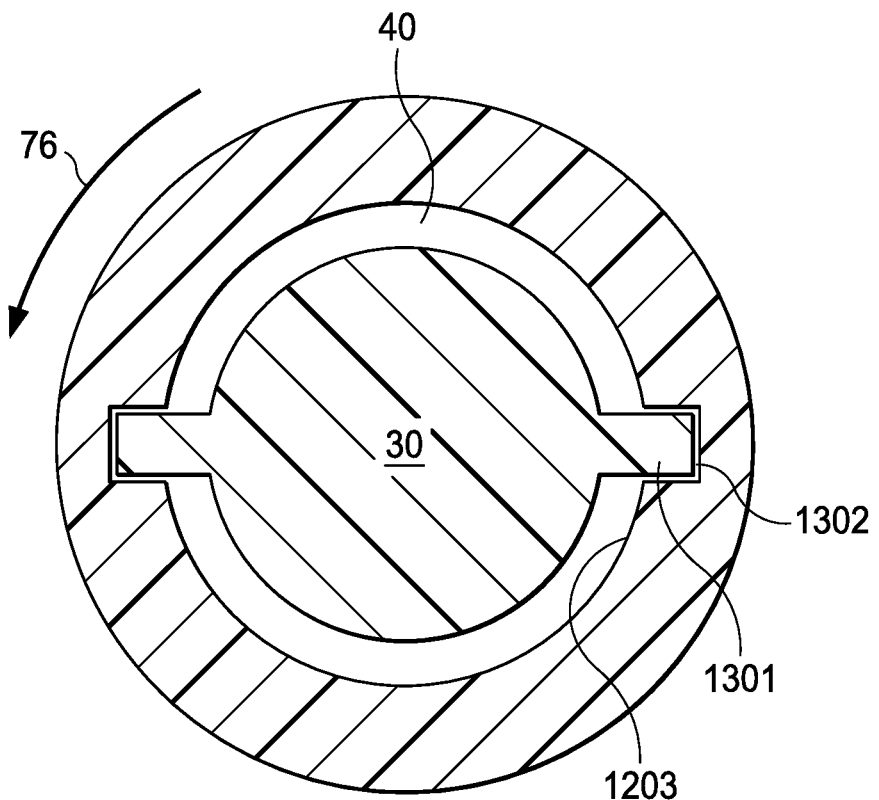
FIG. 15 is a schematic of an example non-circular plunger-bore interface.

In some implementations of the IOL injector 10 described herein, in order to increase stability of the plunger 30 within the bore 40, an axial interface between the plunger 30 and the bore 40 may have a non-circular cross-section, to prevent rolling of the plunger within the bore in the direction of arrow 76. FIG. 15 is a schematic of an example non-circular plunger-bore interface, as viewed a transverse plane of the plunger 30 and the bore 40. For example, in the plunger body 200 of the plunger, the plunger 30 may have wings 1301 that extend along the length, or a portion of the length, of the plunger 30, and are adapted to interface with grooves 1302 along the length, or a portion of the length, of the internal surface 1203 of the bore 40. Other non-circular shapes are possible and identifiable by skilled persons upon reading of the present disclosure, such as a D-shaped transverse cross-section.

The IOL injector 10 having the lever-driven rack and pinion system may be adapted to be held in a tripod grip, for example with thumb in contact with a side of the collapsible portion, a middle finger on contact with the opposite side of the collapsible portion, and the depressible surface 610 of the lever 605 is adapted to be depressible by an index finger of a user. This may provide more stability for users to hold the device steady during the delivery of the IOL 10 into an eye.

Various implementations of the IOL injector described herein and within the scope of the present disclosure may be adapted to deliver an IOL base and/or an IOL optic of a multi-piece IOL, or a one-piece IOL. Various implementations of the IOL injectors and associated methods described herein may be used with an IOL base and/or the optic that are manually loaded into the IOL injector by a user or pre-loaded there prior to delivery by a user.

Non-limiting examples of IOL injectors that may be adapted for use with the IOL compressor as described herein include those described in U.S. Pat. No. 7,156,854 and U.S. Patent Application Publication No. 2016/0256316, the disclosures of each being incorporated herein by reference in their entireties.

Advantages of the IOL injectors described herein include but are not limited to the following. The lever-driven rack and pinion system described herein, optionally including the ribbed damping mechanism described herein, provides a solution to generate axial forward motion for an IOL in a smooth and controlled manner. The lever-driven rack and pinion mechanism may be adapted to provide mechanical advantage using a lever-driven gear system to drive the plunger forward in one direction. The ribbed damping mechanism provides improved control for a better surgical experience. The collapsible feature improves ergonomics by reducing the overall length of the device.

The initial movement of the IOL to the dwell position is achieved through a collapsing slide. This feature shortens the overall length of the device and improves the usability and ergonomics of the device. The shorter device fits better in one hand and provides a better center of mass for the user controlling hand over existing IOL injectors having either traditional syringe or tripod grips.

For delivery of the IOL into the eye, using the lever-driven rack and pinion system, the IOL injector may be held in a tripod grip, also known as a pencil grip, with the user pushing the lever with their index finger, using fewer muscles than a typical syringe type grip.

The lever-driven rack and pinion system may in several implementations use lever pressing combined with pinions, sometimes used as gears to provide additional mechanical advantage, gears to actuate axial movement of the plunger, rather than some existing IOL injectors that use traditional syringe-type mechanisms to apply direct axial force to inject the IOL. In traditional syringe or push-type mechanisms, the force applied by the user on the plunger is typically directly proportional to how quickly the IOL travels. By adapting the IOL delivery mechanism using the lever-driven rack and pinion system as described herein, there is mechanical advantage gained coupled with more controlled and consistent IOL movement. This consistency mitigates incidences of sudden IOL ejection as well as reduces user fatigue associated with applying a constant force for a longer period of time. The IOL injector can be held using one hand in a pencil grip fashion. The lever is actuated by pressing and releasing it several times in order to advance the IOL. In some implementations wherein the IOL is preloaded aids in maintaining the sterility of the IOL injector and IOL throughout the procedure as well as removes a user preparation step.

The above disclosed subject matter is to be considered illustrative, and not restrictive, and the appended claims are intended to cover all such modifications, enhancements, and other implementations which fall within the true spirit and scope of the present disclosure. Thus, to the maximum extent allowed by law, the scope of the present disclosure is to be determined by the broadest permissible interpretation of the following claims and their equivalents and shall not be restricted or limited by the foregoing detailed description.

The invention claimed is:

1. An intraocular lens (IOL) injector having a collapsible injector body, the IOL injector comprising:
   a main body having a proximal end, a distal end, and a distal portion including the distal end; and
   a collapsible portion forming a telescoping cylinder and having at least a first sleeve having a proximal end and a distal end and a second sleeve slideably coupled with the first sleeve and formed from the distal portion of the main body and having a proximal end and a distal end;
   wherein, in an uncollapsed configuration, the distal end of the second sleeve is adjacent to the proximal end of the first sleeve, and, in a collapsed configuration, the distal end of the second sleeve is adjacent to the distal end of the first sleeve.

2. The IOL injector of claim 1, wherein the IOL injector further comprises:
   a nozzle having a proximal end and a distal end, the proximal end coupled to the distal end of the first sleeve of the collapsible portion, the nozzle further having an IOL storage location and an IOL dwell position distal to the IOL storage location;
      a bore having a longitudinal axis extending from the proximal end of the main body to the distal end of the nozzle; and
   a plunger movably coupled concentrically within the injector body and aligned within the bore, the plunger having a plunger tip adapted to contact an IOL;
   wherein, in the uncollapsed configuration, the plunger tip has a first position proximally adjacent to the IOL storage location, and, in the collapsed configuration, the plunger tip has a second position proximally adjacent to the IOL dwell position.

3. The IOL injector of claim 1, wherein the IOL injector has a length which, in the collapsed configuration, is 10 to 20% shorter than in the uncollapsed configuration.

4. The IOL injector of claim 1, wherein the second sleeve is slideably coupled concentrically within the first sleeve.

5. The IOL injector of claim 1, wherein the first sleeve is slideably coupled concentrically within the second sleeve.

6. An intraocular lens (IOL) injector having a lever-driven rack and pinion system, the IOL injector comprising:
   an injector body having:
      a main body having a proximal end and a distal end;
      a nozzle having a proximal end and a distal end, the proximal end of the nozzle coupled to the distal end of the main body; and
      a bore having a longitudinal axis extending from the proximal end of the main body to the distal end of the nozzle;
   at least one pinion having a plurality of teeth;
   a lever having:
      a distal end;
      a pivot point located between the proximal end of the lever and the distal end and rotatably coupled to the injector body to allow a rotational movement of the lever about the pivot point;
      a depressible surface accessible to a user and located between the pivot point and the distal end of the lever; and
      a proximal end having an arcuate rack having a plurality of teeth adapted to interface with a plurality of teeth of one pinion and rotationally move the pinion in response to movement of the arcuate rack; and
   a plunger movably coupled concentrically within the injector body and aligned within the bore, the plunger having:
      a plunger body having a proximal end and a distal end and further having a plunger rack including a plurality of teeth adapted to interface with a plurality of teeth of one pinion and the plunger rack further adapted to be linearly moveable towards the distal end of the nozzle in response to rotational movement of one pinion,
      a plunger rod having a proximal end and a distal end, the proximal end of the plunger rod coupled to the distal end of the plunger body; and
      a plunger tip formed at the distal end of the plunger rod and adapted to contact an IOL and move the IOL from a dwell position in response to a depression of the surface of the lever.

7. The IOL injector of claim 6 comprising one pinion, wherein:
   the plurality of teeth of the arcuate rack are adapted to interface with the plurality of teeth of the pinion,
   the plurality of teeth of the plunger rack are adapted to interface with the plurality of teeth of the pinion,
   in response to the depression of the depressible surface of the lever, the lever is adapted to rotate about the pivot point in a first rotational direction and move the plurality of teeth of the arcuate rack in the first rotational direction, and the pinion is adapted to rotate in a second rotational direction, and
   the plunger rack is adapted to be linearly moveable towards the distal end of the nozzle in response to the rotational movement of the pinion in the second rotational direction.

8. The IOL injector of claim 6, comprising two pinions, wherein:
   the plurality of teeth of the arcuate rack are adapted to interface with a plurality of teeth of a first pinion;
   the plurality of teeth of the first pinion are adapted to interface with a plurality of teeth of a second pinion
   the plurality of teeth of the plunger rack are adapted to interface with the plurality of teeth of the second pinion,
   in response to the depression of the depressible surface of the lever, the lever is adapted to rotate about the pivot point in a first rotational direction and move the plurality of teeth of the arcuate rack in the first rotational direction, the first pinion is adapted to rotate in a second rotational direction, and the second pinion is adapted to rotate in the first rotational direction, and
   the plunger rack is adapted to be linearly movable towards the distal end of the nozzle in response to the rotational movement of the second pinion in the first rotational direction.

9. The IOL injector of claim 8, wherein:
   the first pinion further comprises a pawl;
   the second pinion further comprises a ratchet; and
   the pawl is adapted to interface with the ratchet to prevent movement of the plunger rack toward the proximal end of the nozzle.

10. The IOL injector of claim 8, wherein:
    the first pinion has a circumference $R_1$;
    the second pinion has a circumference $R_2$;
    and the ratio of the value of $R_2$ to $R_1$ is from 1:1 to 1:5.

11. The IOL injector of claim 6, further comprising a reset spring having a first end coupled to the lever and a second end coupled to the injector body, the lever adapted to rotate in a first rotational direction in response to a depression of the depressible surface of the lever, and the reset spring adapted to rotate the lever in a second rotational direction opposite the first rotational direction.

12. The IOL injector of claim 6, wherein:
the nozzle has an IOL storage location and an IOL dwell position, the IOL dwell position distal to the IOL storage location,
a distance between the IOL dwell position and the distal end of the nozzle has a length r, and
the plunger rack is adapted to move a distance of length r in response to 1 to 10 depressions of the lever.

13. The IOL injector of claim 6, wherein the injector body is collapsible and the IOL injector comprises:
a main body having a proximal end, a distal end, and a distal portion including the distal end; and
a collapsible portion forming a telescoping cylinder and having at least a first sleeve having a proximal end and a distal end and a second sleeve slideably coupled with the first sleeve and formed from the distal portion of the main body and having a proximal end and a distal end;
wherein, in an uncollapsed configuration, the distal end of the second sleeve is adjacent to the proximal end of the first sleeve, and, in a collapsed configuration, the distal end of the second sleeve is adjacent to the distal end of the first sleeve.

14. The IOL injector of claim 13, wherein the plurality of teeth of the plunger rack interface with the plurality of teeth of the pinion when the IOL injector is in the collapsed configuration, but not when the IOL injector is in the uncollapsed configuration.

15. The IOL injector of claim 6, wherein the plunger body comprises a flange adapted to contact the proximal end of the plunger body, wherein the plunger body is adapted to move axially in response to an axial force applied to the flange and the plunger tip is adapted to move the IOL from a storage location to the dwell position in response to the axial force applied to the flange.

16. The IOL injector of claim 6, wherein the IOL injector further comprises a ribbed damping mechanism having at least one rib on the plunger body and at least one rib on an interior wall of the bore, wherein the at least one rib on the plunger is adapted to contact the at least one rib on the interior wall and to provide a frictional resistance to axial movement of the plunger.

17. The IOL injector of claim 16, wherein one or more of the ribs on the plunger body forms a ridge and one or more ribs on the interior wall forms a ridge-engaging tooth, wherein the ridge and the ridge-engaging tooth are adapted to prevent movement of the plunger toward the proximal end of the main body of the IOL injector.

18. The IOL injector of claim 16, wherein one or more of the ribs on the interior wall forms a ridge and one or more ribs on the plunger forms a ridge-engaging tooth, wherein the ridge and the ridge-engaging tooth are adapted to prevent movement of the plunger toward the proximal end of the main body of the IOL injector.

19. The IOL injector of claim 6, wherein the IOL injector is adapted to separately inject an IOL base, an IOL optic, or both.

20. The IOL injector of claim 6, wherein the IOL injector is adapted to concurrently inject an IOL base and an IOL optic.

* * * * *